US008826448B2

(12) United States Patent
Peckover

(10) Patent No.: US 8,826,448 B2
(45) Date of Patent: *Sep. 2, 2014

(54) SYSTEM, METHOD AND APPARATUS FOR ELECTRONICALLY PROTECTING DATA AND DIGITAL CONTENT

(71) Applicant: DT Labs, LLC, Carroliton, TX (US)

(72) Inventor: Douglas Peckover, Dallas, TX (US)

(73) Assignee: DT Labs, LLC, Carrollton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/061,649

(22) Filed: Oct. 23, 2013

(65) Prior Publication Data

US 2014/0053240 A1 Feb. 20, 2014

Related U.S. Application Data

(63) Continuation of application No. 13/971,708, filed on Aug. 20, 2013, now abandoned, which is a continuation of application No. 13/563,379, filed on Jul. 31, 2012, now Pat. No. 8,543,806, which is a continuation of application No. 13/070,369, filed on Mar. 23, 2011, now Pat. No. 8,261,058, which is a continuation of application No. 11/378,549, filed on Mar. 16, 2006, now Pat. No. 7,937,579.

(60) Provisional application No. 60/662,562, filed on Mar. 16, 2005, provisional application No. 60/773,518, filed on Feb. 15, 2006.

(51) Int. Cl.
*G06F 7/04* (2006.01)
*G06F 11/30* (2006.01)

(52) U.S. Cl.
USPC .......................................... 726/26; 713/193

(58) Field of Classification Search
USPC ............... 713/164–167, 189, 193; 726/26–30
See application file for complete search history.

(56) References Cited

U.S. PATENT DOCUMENTS 4,701,840 A * 10/1987 Boebert et al. ................... 726/4
5,644,710 A * 7/1997 Johnson et al. ................. 726/21
(Continued)

FOREIGN PATENT DOCUMENTS

JP 2005-092608 A 4/2005
KR 10-2005-0053569 A 6/2005

OTHER PUBLICATIONS

International Search Report and Written Opinion for PCT/US2009/059601, Jan. 27, 2010.

(Continued)

*Primary Examiner* — Darren B Schwartz
(74) *Attorney, Agent, or Firm* — Ascenda Law Group, PC

(57) ABSTRACT

A system, method and apparatus for protecting sensitive data in a file that has been replaced with pointer(s) for each sensitive data. The sensitive data items are protected by restricting subsequent access to and use of the sensitive data items via the pointers by: receiving a first request for data stored in a file on the data storage, determining whether the requested data includes at least one of the pointers, providing the requested data whenever the requested data does not include any of the pointers, and performing the following steps whenever the requested data includes at least one of the pointers: sending a second request containing the pointer(s) included in the requested data to the server that authenticates the second request, denying the first request whenever the authentication fails, and receiving and providing the extracted data item(s) corresponding to the pointer(s) included in the requested data whenever the authentication succeeds.

8 Claims, 32 Drawing Sheets

(56) References Cited

U.S. PATENT DOCUMENTS

| | | |
|---|---|---|
| 5,768,384 A | 6/1998 | Berson |
| 5,999,943 A | 12/1999 | Nori et al. |
| 6,292,657 B1 | 9/2001 | Laursen et al. |
| 6,409,082 B1 | 6/2002 | Davis et al. |
| 6,442,276 B1 | 8/2002 | Doljack |
| 6,547,137 B1 | 4/2003 | Begelfer et al. |
| 6,718,361 B1 | 4/2004 | Basani et al. |
| 6,753,830 B2 | 6/2004 | Gelbman |
| 6,877,094 B1 | 4/2005 | DiGiorgio et al. |
| 6,976,165 B1* | 12/2005 | Carpentier et al. ........... 713/165 |
| 6,996,543 B1 | 2/2006 | Coppersmith et al. |
| 7,200,761 B1 | 4/2007 | Freeman et al. |
| 7,207,481 B2 | 4/2007 | Barenburg et al. |
| 7,222,791 B2 | 5/2007 | Heilper et al. |
| 7,303,123 B2 | 12/2007 | Roberts |
| 7,391,865 B2 | 6/2008 | Orsini et al. |
| 7,395,425 B2 | 7/2008 | Nakano et al. |
| 7,407,107 B2 | 8/2008 | Engestrom et al. |
| 7,464,268 B2 | 12/2008 | Kent, Jr. et al. |
| 7,530,099 B2 | 5/2009 | Flurry et al. |
| 7,542,942 B2 | 6/2009 | Peart et al. |
| 7,739,301 B2* | 6/2010 | Bojinov et al. ............... 707/782 |
| 7,778,903 B2 | 8/2010 | Weichert et al. |
| 7,784,681 B2 | 8/2010 | Silverbrook et al. |
| 7,920,050 B2 | 4/2011 | Juels et al. |
| 7,937,579 B2 | 5/2011 | Peckover |
| 7,996,503 B2 | 8/2011 | Van Vleck et al. |
| 2002/0103811 A1 | 8/2002 | Fankhauser et al. |
| 2002/0103881 A1 | 8/2002 | Granade et al. |
| 2002/0144153 A1* | 10/2002 | LeVine et al. ................ 713/201 |
| 2002/0147929 A1* | 10/2002 | Rose ............................ 713/201 |
| 2003/0037248 A1* | 2/2003 | Launchbury et al. ......... 713/193 |
| 2003/0061512 A1 | 3/2003 | Flurry et al. |
| 2003/0110169 A1 | 6/2003 | Zuili et al. |
| 2003/0135465 A1 | 7/2003 | Lee et al. |
| 2004/0010602 A1 | 1/2004 | Van Vleck et al. |
| 2004/0078596 A1 | 4/2004 | Kent, Jr. et al. |
| 2004/0111639 A1 | 6/2004 | Schwartz et al. |
| 2004/0128556 A1* | 7/2004 | Burnett ......................... 713/201 |
| 2004/0143743 A1* | 7/2004 | Margolus et al. ............. 713/176 |
| 2005/0010764 A1* | 1/2005 | Collet et al. .................. 713/165 |
| 2005/0033686 A1 | 2/2005 | Peart et al. |
| 2005/0061878 A1 | 3/2005 | Barenburg et al. |
| 2005/0091402 A1* | 4/2005 | Satagopan et al. ............ 709/245 |
| 2005/0091545 A1 | 4/2005 | Soppera |
| 2005/0108044 A1 | 5/2005 | Koster |
| 2005/0193198 A1 | 9/2005 | Livowsky |
| 2005/0210072 A1* | 9/2005 | Bojinov et al. ............... 707/200 |
| 2005/0222961 A1 | 10/2005 | Staib et al. |
| 2005/0258234 A1 | 11/2005 | Silverbrook et al. |
| 2006/0033608 A1 | 2/2006 | Juels et al. |
| 2006/0059547 A1 | 3/2006 | Deloume |
| 2006/0072611 A1 | 4/2006 | Kamperman et al. |
| 2006/0075228 A1 | 4/2006 | Black et al. |
| 2006/0087682 A1 | 4/2006 | Lee |
| 2006/0107058 A1* | 5/2006 | Lewis et al. ................... 713/176 |
| 2006/0168644 A1 | 7/2006 | Richter et al. |
| 2006/0174329 A1 | 8/2006 | Dublish |
| 2006/0175401 A1 | 8/2006 | Roberts |
| 2006/0212698 A1 | 9/2006 | Peckover |
| 2007/0143853 A1 | 6/2007 | Tsukamoto |
| 2007/0300304 A1 | 12/2007 | Lindgren |
| 2008/0209550 A1 | 8/2008 | Di Iorio |
| 2008/0209576 A1 | 8/2008 | Nooning |
| 2008/0222706 A1 | 9/2008 | Renaud et al. |
| 2008/0301818 A1 | 12/2008 | Sedimeyer |
| 2009/0025094 A1 | 1/2009 | York et al. |
| 2009/0260087 A1 | 10/2009 | Ishida et al. |
| 2009/0293109 A1 | 11/2009 | Chu |
| 2010/0005509 A1 | 1/2010 | Peckover |
| 2010/0106645 A1 | 4/2010 | Peckover |

OTHER PUBLICATIONS

Karygiannis et al., "Guidelines for Securing Radio Frequency Identification (RFID) Systems", National Institute of Standards and Technology, U.S. Department of Commerce, (2007) Special Publication 800-98, pp. 1-154.

* cited by examiner

| Emp# | SSN | DOB | Name | Address | City | State | Zip |
|---|---|---|---|---|---|---|---|
| 0312948 | 756982766 | 1975/09/13 | Julie J. Holmes-Bridges | 2532 Victory Ln. | Richardson | Tx | 75080 |
| 4568783 | 456112763 | 1972/10/24 | Daniel P. Bridges | 2532 Victory Ln. | Richardson | Tx | 75080 |
| 9834753 | 923847567 | 1960/04/02 | Phillip M. Jones | 8735 Brown Way | Richardson | Tx | 75085 |
| 9283457 | 928347566 | 1980/02/06 | Candace R. Miles | 8772 Crown Dr. #431 | Garland | Tx | 75044 |
| 0968778 | 892346557 | 1974/07/16 | Stephen D. Buoy | 9847 Parker Rd. | Plano | Tx | 75024 |
| 9873442 | 879455239 | 1985/11/30 | Michael M. Bushey | 4676 Montford Pl. #7 | Garland | Tx | 75048 |
| 6982352 | 473490838 | 1940/05/25 | Bobby K. Torez | 3578 Merlin Ave. | Richardson | Tx | 75082 |
| 6752393 | 328788759 | 1901/07/26 | Robert B. Niles | 8480 Northgate Rd. | Plano | Tx | 75075 |
| 5723987 | 897589760 | 1972/03/11 | Martha P. Gonzalez | 7456 Custer Pkwy. | Richardson | Tx | 75080 |
| 4987656 | 984987454 | 1972/01/27 | Hope R. Jackson | 4678 Masters Ln. #575 | Richardson | Tx | 75082 |

FIG. 3

┌─────────────────────────────────────────────────────┐
│ HR Medical Claim System                    _ □ ✕    │
├─────────────────────────────────────────────────────┤
│ │      <<      │    1 of 10    │      >>      │    │
├─────────────────────────────────────────────────────┤
│        Emp#   0312948                               │
│         SSN   756-98-2766                           │
│         DOB   1975/09/13                            │
│        Name   Julie J. Holmes-Bridges               │
│     Address   2532 Victory Ln.                      │
│        City   Richardson                            │
│       State   Tx                                    │
│         Zip   75080                                 │
├─────────────────────────────────────────────────────┤
│ Date       │ Code │ Description          │   Amount │
│ 2001/12/24 │ CT   │ Carpal Tunnel        │   500.00 │
│ 2003/11/16 │ LI   │ Laceration Injury    │   450.00 │
│ 2005/05/06 │ BT   │ Blunt Trama          │  1654.00 │
│                                                     │
│ Total                                       2604.00 │
└─────────────────────────────────────────────────────┘

FIG. 21

HR Medical Claim System  □ ☒ ✕

[<<]  1 of 10  [>>]

| Emp# | 0312948 |
|---|---|
| SSN | 649-04-516 |
| DOB | 9226944cad |
| Name | 90a668d27095fbd68d6c99e83bfef978 |
| Address | 03237237 82a58124108 1 1cf99850f5a1a40e015 |
| City | Richardson |
| State | Tx |
| Zip | 75080 |

| Date | Code | Description | Amount |
|---|---|---|---|
| 2001/12/24 | CT | Carpal Tunnel | 500.00 |
| 2003/11/16 | LI | Laceration Injury | 450.00 |
| 2005/05/06 | BT | Blunt Trama | 1654.00 |

Total   2604.00

↗ 2200

---

HR Medical Claim System  □ ☒ ✕

[<<]  1 of 10  [>>]

| Emp# | 0312948 |
|---|---|
| SSN | 756-98-2766 |
| DOB | 1975/09/13 |
| Name | Julie J. Holmes-Bridges |
| Address | 2532 Victory Ln. |
| City | Richardson |
| State | Tx |
| Zip | 75080 |

| Date | Code | Description | Amount |
|---|---|---|---|
| 2001/12/24 | CT | Carpal Tunnel | 500.00 |
| 2003/11/16 | LI | Laceration Injury | 450.00 |
| 2005/05/06 | BT | Blunt Trama | 1654.00 |

Total   2604.00

Microsoft Excel- Mortgage Fees Analysis

File  Edit  View  Insert  Format  Tools  Data  Window  Theft Proof Data  Help

B6 — Darryl L. Smith

Mortgage Fees Analysis

| | B | 2300 C | 2302 | 2304 D | 2306 E | 2308 F | 2310 G | 2312 H | 2314 I | 2316 J |
|---|---|---|---|---|---|---|---|---|---|---|
| 1 | | | | | | | | | | |
| 2 | | | | | | | | | | |
| 3 | | | Loan Number | | | | | | | |
| 4 | | Name | | SSN | Credit Score | Monthly Payment | Overdue Payments | Late Charges | Other Charges | Total Charges |
| 5 | | | | | | | | | | |
| 6 | | Darryl L. Smith | 2623762 | 545-12-7683 | 740 | 3,441.60 | 6,883.20 | 172.08 | | 172.08 |
| 7 | | Brendan R. Cousins | 2778413 | 165-73-1546 | 587 | 1,247.58 | | | 25.00 | 25.00 |
| 8 | | Lynn B Crosby | 2933064 | 254-15-6567 | 603 | 1,477.02 | | | | - |
| 9 | | Frank B Wrong | 3087715 | 476-17-1543 | 688 | 2,695.92 | | | 110.00 | 110.00 |
| 10 | | William S Bellows | 3242366 | 546-12-5462 | 714 | 3,068.76 | 3,068.76 | | | - |
| 11 | | Thomas A Smart | 3397017 | 435-12-4059 | 711 | 3,025.74 | | 151.29 | | 151.29 |
| 12 | | Terry F Young | 3551668 | 512-41-0583 | 634 | 1,921.56 | | | | - |

Sensitive data that must be protected.

Data that does not contain sensitive data and may be accessed by anymore.

FIG. 23

Secure Server — 204

Microsoft Excel- Mortgage Fees Analysis

File  Edit  View  Insert  Format  Tools  Data  Window  Theft Proof Data  Help

Mortgage Fees Analysis

| | A | B | C | D | E | F | G | H | I | J |
|---|---|---|---|---|---|---|---|---|---|---|
| 1 | | | | | | | | | | |
| 2 | | | | | | | | | | |
| 3 | | | | | | | | | | |
| 4 | | | | | Credit Score | Monthly Payment | Overdue Payments | Late Charges | Other Charges | Total Charges |
| 5 | | | | | 740 | 3,441.60 | 6,883.20 | 172.08 | | 172.08 |
| 6 | | | | | 587 | 1,247.58 | | | 25.00 | 25.00 |
| 7 | | | | | 603 | 1,477.02 | | | | - |
| 8 | | | | | 688 | 2,695.92 | | | 110.00 | 110.00 |
| 9 | | | | | 714 | 3,025.74 | | | | - |
| 10 | | | | | 711 | 3,068.76 | | | | |
| 11 | | | | | 634 | 1,921.56 | 3,068.76 | 151.29 | | 151.29 |
| 12 | | | | | | | | | | - |

FIG. 24B

SYSTEM, METHOD AND APPARATUS FOR ELECTRONICALLY PROTECTING DATA AND DIGITAL CONTENT

PRIORITY CLAIM

This patent application is a continuation application of U.S. patent application Ser. No. 13/971,708 filed Aug. 20, 2013 and entitled "System, Method and Apparatus for Electronically Protecting Data and Digital Content", which is a continuation application of U.S. patent application Ser. No. 13/563,379 filed on Jul. 31, 2012 and entitled "System, Method and Apparatus for Electronically Protecting Data and Digital Content", now U.S. Pat. No. 8,543,806, which is a continuation application of U.S. patent application Ser. No. 13/070,369 filed on Mar. 23, 2011 and entitled "System, Method and Apparatus for Electronically Protecting Data and Digital Content", now U.S. Pat. No. 8,261,058, which is a continuation application of U.S. patent application Ser. No. 11/378,549 filed on Mar. 16, 2006 and entitled "System, Method and Apparatus for Electronically Protecting Data and Digital Content", now U.S. Pat. No. 7,937,579, which is a non-provisional application of U.S. provisional patent application 60/662,562 filed on Mar. 16, 2005 and entitled "Managing Personally Identifiable Information" and U.S. provisional patent application 60/773,518 filed on Feb. 15, 2006 and entitled "Managing Personally Identifiable Information," all of which are hereby incorporated by reference in their respective entireties.

FIELD OF THE INVENTION

The present invention relates generally to the field of computerized data storage retrieval and, more particularly, to a system, method and apparatus for electronically protecting data and digital content.

BACKGROUND OF THE INVENTION

We live in uncertain times. There is no shortage of examples of how the digital age that we live in is becoming increasingly more dangerous for both individuals and companies:

- According to the Federal Trade Commission, identity theft is number one crime in America and affects almost 20 thousand new victims each day.
- In 2005 alone, data belonging to more than 60 million Americans was hacked, was on lost backup tapes, or was in computers that were stolen.
- Wells Fargo lost a single laptop and is said to have paid more than $10 million notifying its customers under California's SB-1386 regulation.
- An auditor working for McAfee lost a CD with personal information containing 9,000 of its employees. McAfee's market valuation immediately dropped $600 million.
- Outsourcing to countries like India is tempting as a way to reduce costs, but data stolen overseas is being used to blackmail U.S. companies.
- Compliance costs for Sarbanes-Oxley are so high that they are measured as a percent of total revenue.
- Software, music, and DVD pirating in countries like China is making a mockery of copyright laws.

All of these examples have one thing in common—the need to protect data has become extremely urgent. Current technologies like encryption, SSL, and VPNs have been shown to be only partially adequate. Security experts warn that data loss and theft is "just going to continue."

Identity management systems, encryption, SSL, VPN's, and other security products are all part of a necessary strategy to protect sensitive data. There is still, however, a gaping hole in this strategy—how can sensitive data be protected when these tools fail? How can firms control sensitive data when a laptop is stolen? Or when data is shared with a trading partner and that trading partner's servers are compromised? Or when a trusted employee becomes a rogue employee? Or when the sensitive data is overseas at an unknown location? Or when copyright material has been cracked and copied in China. Current products have failed to protect against these problems, and the Sarbanes-Oxley Act now holds public company officers personally responsible for the consequences.

Just twenty years ago, disk storage space was so expensive that many companies saved money by not storing the "19" as a part of the year (and the resulting Y2K problem cost companies billions of dollars). Today, disk storage space costs just 30¢ a gigabyte and continues to fall at a rate predicted by Moore's Law. The falling cost of collecting, storing, and transmitting data is the reason why data and digital content problems are "just going to continue", perhaps at an accelerated rate. This is compounded by the fact that the U.S. is moving from a manufacturing economy to a services economy, and more and more content is being stored in digital form. This is further complicated by an increasing dependence on portable devices and types of media that are easier to lose or have stolen. Our problems in 2006 might one day be considered to be "the good old days."

Typically, this content is stored and retrieved by an application. Storage is typically a disk drive or semiconductor memory. The application could be a file management system such as a database working with an enterprise human resources system. The application could also be Microsoft® Excel, where the file management system and program are integrated. Other applications could be a DVD device playing a movie, an iPod playing music, a cell phone retrieving phone numbers, or an intelligent navigation system in a car. In all of these examples, the data is stored and retrieved from storage by the application.

Research by Symantec® indicates that an ordinary notebook holds content valued at $972,000 in commercially sensitive data. As devices become more and more portable, it is becoming easier for a perpetrator to steal the storage and application at the same time. Portable devices also increase risks because the application may provide direct access to sensitive data that is stored on central servers.

Current systems fail to address all of the following data security problems:

- The sensitive data or digital content in storage may contain personal, corporate, or copyright content. Anyone with access to storage can make a copy of this.
- If the sensitive content depends on encryption, a "brute force" attack can be used to decrypt it. In the future, quantum computing may make such attacks trivial. Encryption is also problematic because it is difficult to use in many applications. Phil Zimmerman, the creator of PGP, "only uses encryption occasionally."
- Anyone can make a copy of a paper document without leaving any trace that a copy has been made, and without the knowledge or consent of the document's owner. Any number of copies of the original or new document can be made. The same is true for data and digital content, except that it is easier to copy and transmit instantly to any place in the world.

If a person's or entity's money is stolen, it can only be spent once. If a person's or entity's personal or sensitive data is stolen, it can be used any number of times.

It is very difficult to determine if digital content has been accessed or copied.

It is very difficult to determine where a digital copy came from or where it has been sent.

It is very difficult to determine where or when digital content is being used.

It is very difficult to get additional information about what else a perpetrator has copied or is doing.

There is no way to destroy the copied digital content.

There is no way to destroy the device the digital content is stored on.

It is very difficult to collect payment of copyright content that has been copied.

There is no provision for dealing with unknown future threats.

Accordingly there is a need for a system, method and apparatus for electronically storing data and digital content in a way that original and copies of sensitive data can be protected, monitored, controlled, paid for, or even destroyed, as determined by the content owner.

SUMMARY OF THE INVENTION

The present invention provides a system, method and apparatus for electronically storing data and digital content in a way that original content and copies can be protected, monitored, controlled, paid for, or even destroyed, as determined by the content owner. It does not require, but may be further enhanced by existing technologies, including access control systems, encryption, SSL, and VPNs. The present invention is based on the separation of duties and seamless integration at a later time with the proper authentication.

More specifically, the present invention provides a system for protecting sensitive data that includes one or more clients and a server communicably coupled to the one or more clients. Each client has data storage and a processor that extracts the sensitive data from the data storage, sends the extracted data to a server for storage, receives a pointer indicating where the extracted data has been stored and replaces the sensitive data on the data storage with the pointer. The server receives the extracted data from the client, stores the extracted data to a secure storage, generates the pointer and sends the pointer to the client. The client may include a computer, a laptop computer, a handheld computer, a desktop computer, a workstation, a data terminal, a phone, a mobile phone, a personal data assistant, a media player, a gaming console, a security device, a surveillance device or a combination thereof. The server can be communicably coupled to the one or more clients via a computer network, a telecommunications network, a wireless communications link, a physical connection, a landline, a satellite communications link, an optical communications link, a cellular network or a combination thereof.

The present invention also provides an apparatus for protecting sensitive data that includes data storage, a communications interface to a remote server having a secure storage and a processor communicably coupled to the data storage and the communications interface. The processor controls access to the data storage, extracts the sensitive data from the data storage, sends the extracted data to the remote server for storage via the communications interface, receives a pointer indicating where the extracted data has been stored and replaces the sensitive data on the data storage with the pointer.

In addition, the present invention provides a method for protecting sensitive data by extracting the sensitive data from a data storage on a client, sending the extracted data to a server for storage, receiving a pointer indicating where the extracted data has been stored and replacing the sensitive data on the data storage on the client with the pointer. The pointer may include random data that is of a same data type as the sensitive data. Furthermore, the pointer is subsequently used to access the sensitive data after proper authentication. The sensitive data may include personal data, financial data, corporate data, legal data, government data, police data, immigration data, military data, intelligence data, security data, surveillance data, technical data, copyrighted content or a combination thereof. Note that this method can be implemented using a computer program embodied on a computer readable medium wherein the steps are executed by one or more code segments.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which:

FIG. 3 is an example of sensitive fields in client storage in accordance with one embodiment of the present invention;

FIG. 21 illustrates a typical screen that accesses data in accordance with the present invention;

FIG. 22 illustrate how the present invention protects sensitive data in a way that is transparent and seamless to the enterprise database applications;

FIGS. 23, 24A and 24B illustrate protecting sensitive data in Microsoft® Excel® files in accordance with the present invention;

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. The discussion herein relates primarily to the protection of sensitive data or digital content, but it will be understood that the concepts of the present invention are applicable to any client-server system.

The present invention provides a system, method and apparatus for electronically storing data and digital content in a way that original content and copies can be protected, monitored, controlled, paid for, or even destroyed, as determined by the content owner. It does not require, but may be further enhanced by existing technologies, including access control systems, encryption, SSL, and VPNs. The present invention is based on the separation of duties and seamless integration at a later time with the proper authentication.

Figure 1A:
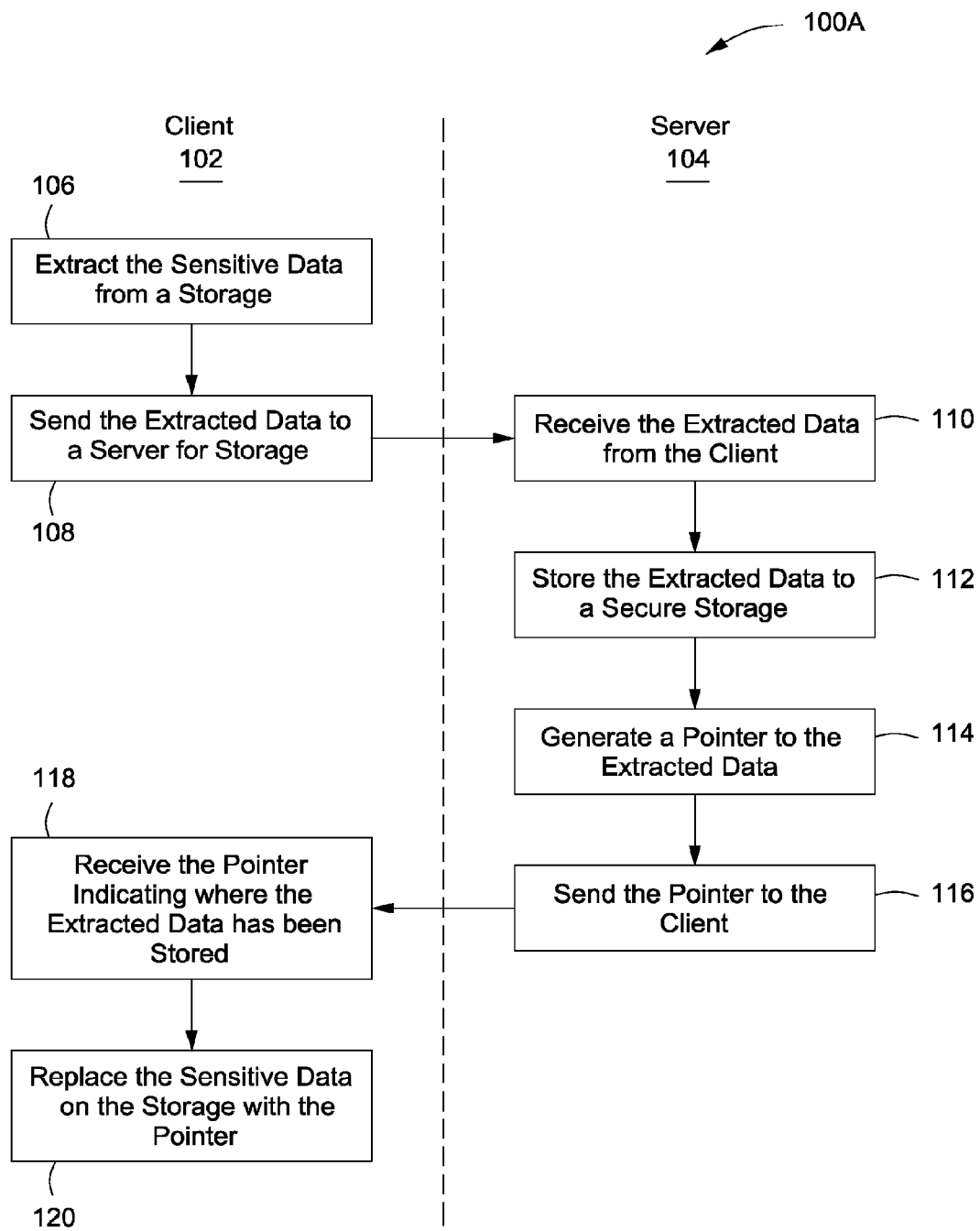
FIGS. 1A and 1B are block diagrams of a method for protecting sensitive data in accordance with one embodiment of the present invention.
Figure 1B:
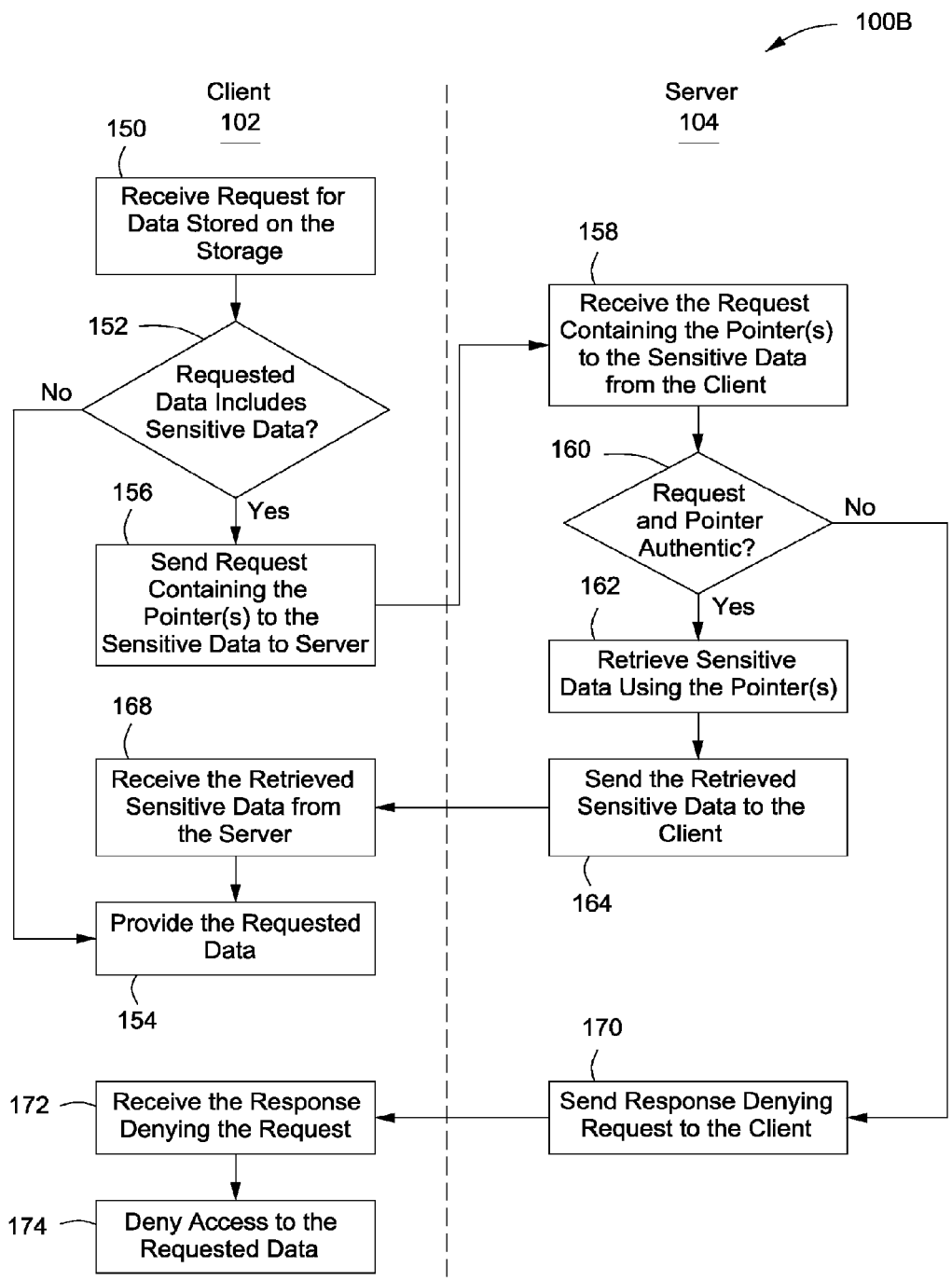

Now referring to FIG. 1A, a block diagram of a method 100a for protecting sensitive data in accordance with one embodiment of the present invention is shown. The sensitive data is extracted from a data storage on a client 102 in block 106 and the extracted data is sent to a server 104 for storage in block 108. The sensitive data may include personal data, financial data, corporate data, legal data, government data, police data, immigration data, military data, intelligence data, security data, surveillance data, technical data, copyrighted content or a combination thereof. The server 104 receives the extracted data from the client 102 in block 110 and stores the extracted data to a secure storage on the server 104 in block 112. One or more pointers to the extracted data are generated in block 114 and the one or more pointers are sent to the client 102 in block 116. The pointer(s) may include random data that is of a same data type as the sensitive data. Furthermore and as shown in FIG. 1B, the pointer(s) is subsequently used to access the sensitive data after proper authentication. The client 102 receives the pointer(s) indicating where the extracted data has been stored in block 118 and then replaces the sensitive data on the data storage on the client 102 with the pointer(s) in block 120. Note that all the methods and processes described herein can be implemented using a computer program embodied on a computer readable medium wherein the steps are executed by one or more code segments. In addition, the communications between the server 104 and the client 102 can be encrypted using well known techniques.

Referring now to FIG. 1B, a block diagram of a method 100b for protecting sensitive data in accordance with one embodiment of the present invention is shown. The client 102 receives a request (first) for data stored on the data storage of the client 102 in block 150 and determines whether the requested data includes the sensitive data in decision block 152. If the requested data does not include the sensitive data, as determined in decision block 152, the requested data is provided in block 154. If, however, the requested data includes the sensitive data, as determined in decision block 152, a request (second) containing the pointer(s) to the sensitive data is sent to the server 104 in block 156 and the request (second) containing the pointer(s) to the sensitive data is received from the client 102 in block 158. If the request and pointer(s) are authentic, as determined in decision block 160, the sensitive data is retrieved using the pointer(s) in block 162 and the retrieved sensitive data is sent to the client 102 in block 164. The client 102 receives the sensitive data from the server 104 in block 168 and provides the requested data in block 154. If, however, the request or the pointer(s) are not authentic, as determined in decision block 160, a response denying the request (second) is sent to the client 102 in block 170. The client 102 receives the response denying the request (second) in block 172 and denies access to the requested data in block 174. An unauthorized attempt to access or use the sensitive data may result in various events being triggered, such as alarms or automatic notifications. Moreover, all these transactions can be logged to create an audit trail. Furthermore, the received sensitive information still may be restricted in that it may only be viewed or used in an authorized application. In other words, the received sensitive information cannot be further transferred or stored. Access to and storage of the sensitive data can be governed by one or more rules.

Figure 2:
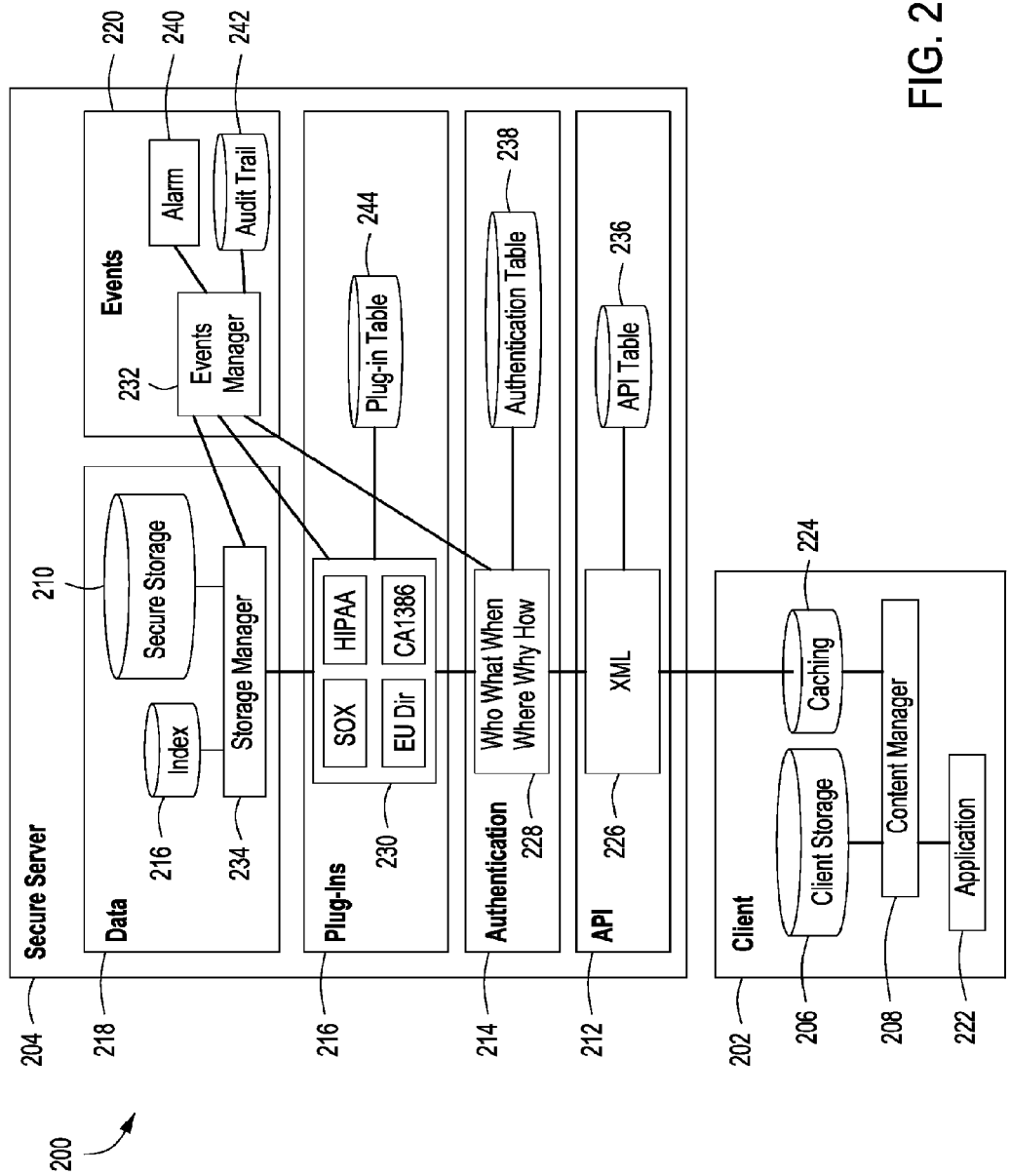
FIG. 2 is a block diagram of a server-client system in accordance with one embodiment of the present invention.

Now referring to FIG. 2, a block diagram of a server-client system 200 in accordance with one embodiment of the present invention is shown. The system 200 includes one or more clients 202 and a server 204 communicably coupled to the one or more clients 202. The client 202 is any device or system that stores sensitive data and then accesses it (e.g., a computer, a laptop computer, a handheld computer, a desktop computer, a workstation, a data terminal, a phone, a mobile phone, a personal data assistant, a media player, a gaming console, a security device, a surveillance device or a combination thereof). This could be anything from a small client like a cell phone right up to a large enterprise system. Each client 202 has client storage 206 and a content manager 208 that extracts the sensitive data from the data storage 206, sends the extracted data to the server 204 for storage, receives a pointer indicating where the extracted data has been stored and replaces the sensitive data on the data storage 206 with the pointer. The server 204 receives the extracted data from the client 202, stores the extracted data to a secure storage 210, generates the pointer and sends the pointer to the client 202. The server 204 can be communicably coupled to the one or more clients 202 via a computer network, a telecommunications network, a wireless communications link, a physical connection, a landline, a satellite communications link, an optical communications link, a cellular network or a combination thereof. Note that communications between the server 204 and the client 202 can be encrypted using well known techniques.

The server 204 includes an application program interface (API) layer 212, an authentication layer 214 coupled to the application program layer 212, a plug-in layer 216 coupled to the authentication layer 214, a data layer 218 coupled to the plug-in layer 216 and an events layer 220 coupled to the data layer 218, the plug-in layer 216 and the authentication layer 214.

The client 202 includes a data storage or client storage 206, one or more applications 222, a communications interface (caching) 224 to a remote server 204 having a secure storage 210, and a content manager 208 communicably coupled to the data storage 206, the one or more applications 222 and the communications interface (caching) 224. The content manager 208 controls access to the data storage 206, extracts the sensitive data from the data storage 206, sends the extracted data to the remote server 204 for storage via the communications interface (caching) 224, receives a pointer(s) indicating where the extracted data has been stored and replaces the sensitive data on the data storage 206 with the pointer(s). The content manager 208 also receives a first request from the one or more applications 222 for data stored on the data storage 206, determines whether the requested data includes the sensitive data and provides the requested data to the one or more applications 222 whenever the requested data does not include the sensitive data. The content manager 208 performs the following steps whenever the requested data includes the sensitive data: sends a second request containing the pointer(s) to the server 204 that authenticates the second request, denies the first request whenever the authentication fails, and receives and provides the sensitive data to the one or more applications 222 whenever the authentication succeeds.

As a result, the present invention removes sensitive data from client storage 206 and transfers it to secure server 204. The content manager 208 is placed between the application 222 and client storage 206 so that the sensitive data can be merged back in a manner that is seamless and transparent to the application 222. The content manager 208 is a new type of client middleware that protects personal, sensitive, and/or copyright content from being used in an unauthorized manner.

The content manager 208 and API layer 212 of the secure server 204 communicate via XML, EDI, or any other communication protocol 226. The API layer 212 also includes an API table 236. Caching 224 may be used to speed up communication, or temporarily store sensitive data when the client 202 is not connected to the secure server 204.

A one-time process extracts the sensitive data in client storage 206 and sends it to secure storage 210 in the secure server 204. In return, the secure server 204 generates one or more pointers that indicate where in secure storage 210 the sensitive data has been stored. This pointer is returned to the content manager 208 and replaces the original sensitive data in client storage 206. One preferred embodiment for this pointer is random data, generated by a plug-in, with the same type as the sensitive data that it is replacing. This pointer is later used by the content manager 208 to get sensitive data from or put sensitive data back into the secure server 204.

After this one-time process, each time the application 222 accesses client storage, the content manager 208 checks to see if the request is for sensitive data. If it is not, then the request is processed in the regular manner. If the access involves sensitive data, then the content manager 208 passes the pointer in client storage 206 to the secure server 204. The sensitive data is got from or put in secure storage according to the rules 228 in the authentication layer 214 and/or plug-ins 230 in the plug-ins layer 216.

The secure server 204 authenticates all client requests in the authentication layer 214, which includes an authentication table 238. Authentication is based on rules 228 that are stored in the secure server 204. For example, a rule could require a specific hardware device be used during business hours with biometric access. Provision is made to integrate the present invention with other access control systems. If authentication fails, then the request is processed by the events manager 232. The events manager 232 provides additional processing capabilities for taking specific protection actions, sending an alarm 240 to notify people, updating audit trails 242, and other event requirements.

An authenticated request is passed to the plug-ins layer 216, which includes plug-in table 244, for processing. Plug-ins 230 provide additional processing capabilities for specific regulations, industries, devices, applications, and other processing needs. The majority of plug-in requests are passed to the data layer 218. Some plug-ins 230 provide additional support for the secure server 204, such as generating random index values for client storage 206, or processing special requests that the owner of the client 202 wants to outsource to a trusted firm, such as storing critical encryption keys in a safe, protected manner. The data layer 218 is controlled by the storage manager 234 where pointers are used to get sensitive data from or put sensitive data in secure storage 210. The data layer 218 also includes an index 246.

Securing Data and Digital Content

Once a table in client storage 206 has been identified as needing the present invention, certain steps are taken to protect it. In the preferred embodiment, the sensitive data in client storage 206 is transferred to secure storage 210 with the following steps:

Referring to FIG. 3, an example of sensitive fields 300 in client storage 206 are shown. In this example, SSN 302, DOB 304, Name 306, and Address 308 need protection; whereas Employee Number 310, City 312, State 314 and Zip Code 316 do not need protection.

Figure 4:
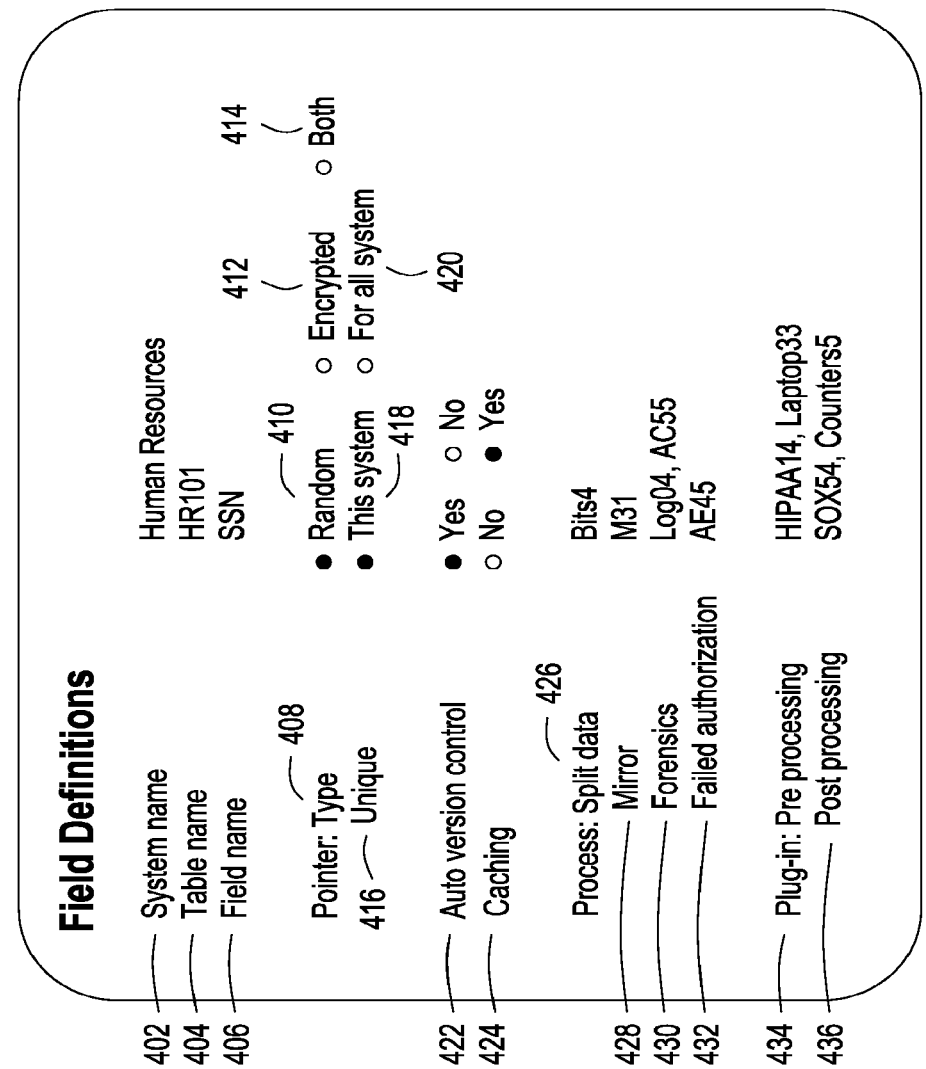
FIG. 4 illustrates a screen that accepts the definitions of the system, table, and fields in client storage that contain sensitive data in accordance with one embodiment of the present invention.

Referring to FIG. 4, a screen 400 accepts the definitions of the system 402, table 404, and fields 406 in client storage 206 that contain sensitive data. These definitions are stored in client storage 206 and/or plug-in table 244.

The sensitive data in the defined fields (402, 404 and 406) are removed from table in client storage 206, the fields in client storage 206 are replaced with random pointers, and the sensitive data is transferred to the secure storage 210.

These same definitions are later used by content manager 208, authentication 214, plug-ins 216, and storage manager 234 to access sensitive data in the index 246 and secure server 204, as well as move it to and from the application 222.

One embodiment of these field definitions can be seen in FIG. 4. The definitions for each sensitive data field include:

The system name 402, such as Human Resources.
The table name 404 in the system, such as HR101.
The field name 406 in the table, such as SSN (Social Security Number).
The pointer type 408, such as random data 410 generated by a plug-in 230, an encrypted value 412, or a combination 414.
If the pointer is to be unique 416 in the current system 418 or for all systems 420 in the secure server 204.

If auto version control 422 is required to make unique copies of the sensitive data in the secure server 204.

If caching 424 on the client 202 is to be used for this field. Answering Yes increases accessibility but may reduce security because client storage 206 and sensitive data from secure storage 210 are on the same device.

If sensitive data fields are to be split 426, and what process to use. For example, the first 4 bits of each byte may be stored in one physical location of secure storage 210 and the other 4 bits of each byte stored on another physical location of secure storage 210. This and other methods obfuscate sensitive data to reduce the chance of a single trusted person having access to all sensitive data.

The process or processes to use if the sensitive data is to be mirrored 428 on more than one physical copy of secure storage 210.

The process or processes to use if additional forensics data 430 is to be stored about this field in secure storage 210. This can be later used to determine the who, what, when, where, and why sensitive data was given.

The process or processes to use if authentication fails 432. Examples include returning a blank value, a dummy value, or taking specific action.

What plug-in(s) 434 to perform before the content manager's 208 request is processed by storage manager 234.

What plug-in(s) 436 to perform after the content manager's 208 request is processed by storage manager 234.

Figure 5:
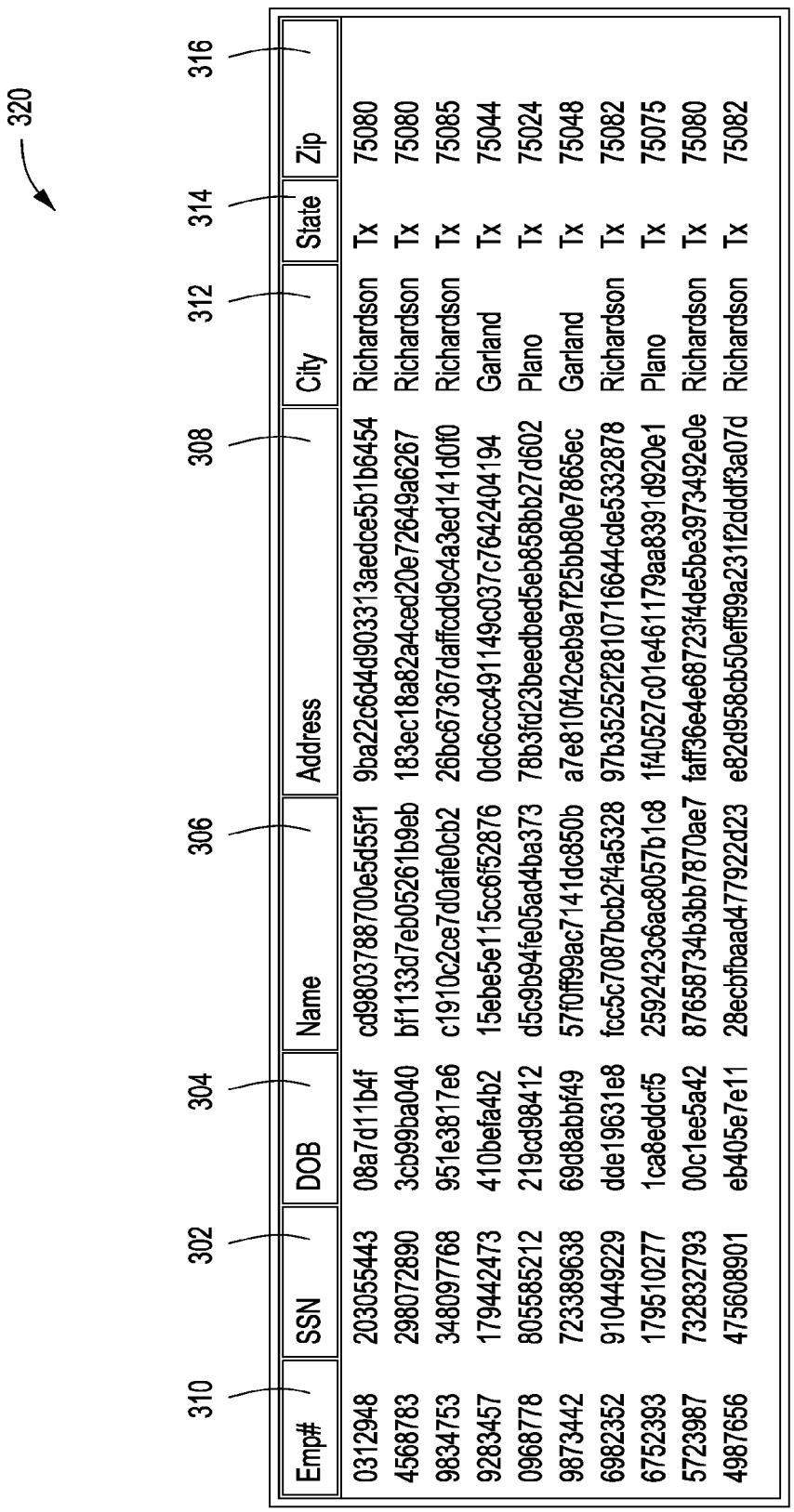
FIG. 5 illustrates an example of FIG. 3 in client storage after conversion in accordance with one embodiment of the present invention.
Figure 6:
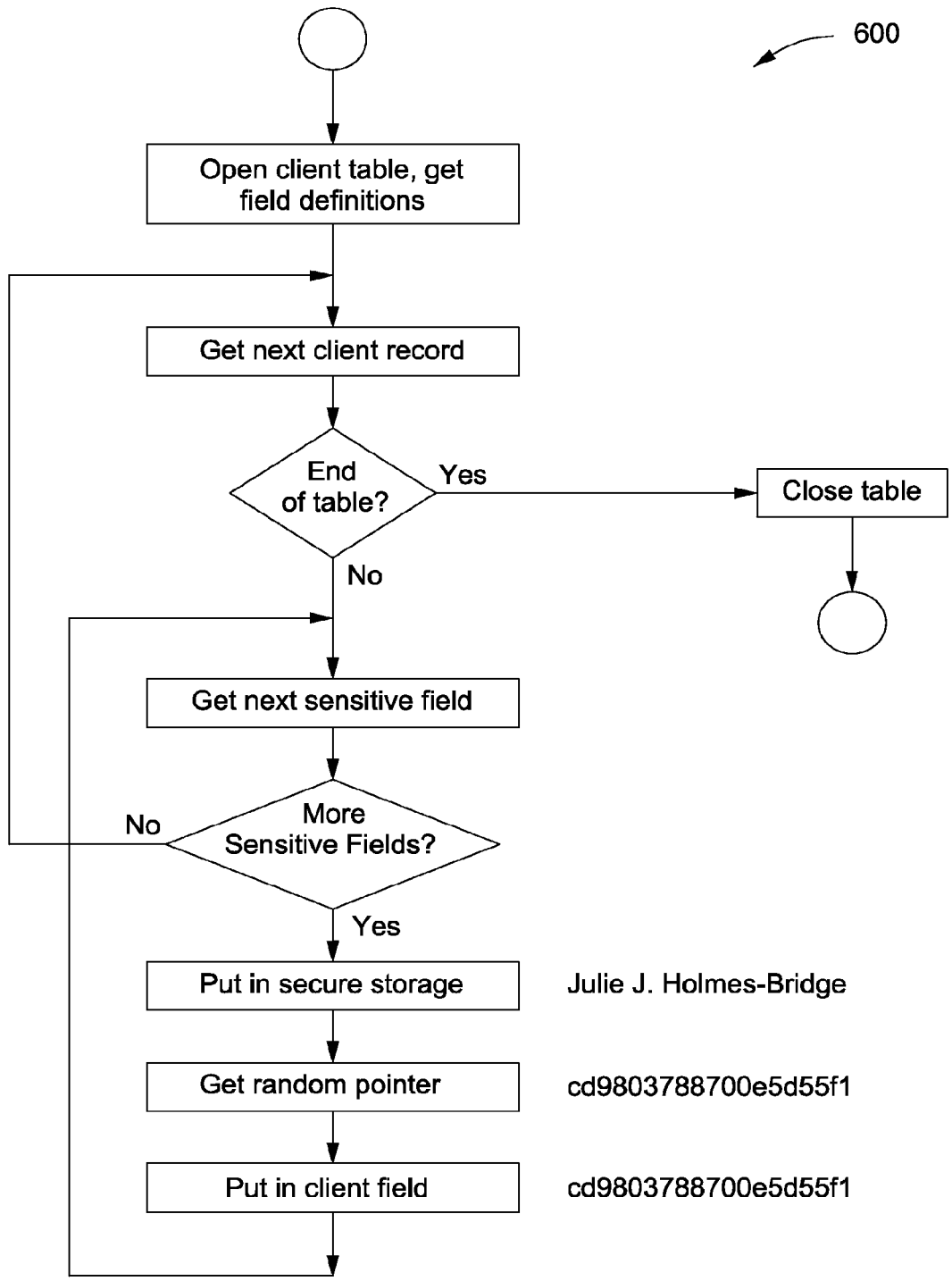
FIG. 6 illustrates the conversion process in accordance with one embodiment of the present invention.

After conversion is complete, the table 320 in client storage 206 is shown in FIG. 5, and the steps 600 taken are shown in FIG. 6. Each record has been examined and the sensitive fields have been moved from client storage 206 to secure storage 218. A plug-in 230 has generated a unique random pointer and passed it back to the content manager 208 where it replaced the original sensitive field. The random pointer was then stored in index in a way that permitted rapid access to the sensitive field. Note that each random pointer in the table used same field type as the sensitive data that it replaced. This made the present invention transparent and seamless to the client application 222.

Client Storage and Communications Security

The table in client storage 206 no longer contains sensitive data and the field values do not use encryption that can be analyzed in any way. The original sensitive data can only be obtained by having content manager 208 pass the random pointer to the secure server 204.

In the preferred embodiment, communication between the client 202 and secure server 204 is an SSL/TLS encryption tunnel.

All data stored in client memory (echo, page files, unallocated space) is single or double encrypted. One preferred embodiment encrypts all data before it is transmitted to the secure server 204. This data is also encrypted on the secure server 204. The use of stream cyphers for encryption allows the encrypted keys to be updated out of order, so that the data is never in the clear on the secure server 204.

Those skilled in the art will add more complex security methods to client storage 206, content manager 208, client memory, communications with secure server 204, and/or secure storage 210.

Content Manager

Content manager 208 seamlessly monitors requests from the application 222 to client storage 206. If the request is for sensitive data, the content manager 208 seamlessly gets sensitive data from or puts sensitive data in secure storage 210.

Content manager 208 also manages all communication with plug-ins 230. This could be to receive new random points, update new software and/or instructions, or any other process.

Client Caching

Caching 224 may be used by client 202 to speed access between the content manager 208 and secure server 204. It can also be used to temporarily store sensitive data from secure storage 210 when the client 202 is not connected to the secure server 204. This enables the application 222 to operate when the user is not connected to the secure server 204, such as on a plane.

Those skilled in the art may use encrypted in-memory caching using a tool such as OpenSSL. One preferred embodiment keeps all cached data in memory in a way that its contents are not permanently stored on the client 202 and are automatically erased when the client device is turned off.

API Layer—How Clients Access the Secure Server

The secure server's 204 API layer 212 communicates with client devices via XML, EDI, or any other communication protocol 226 as defined by API table 236. This enables the present invention to protect sensitive data on any connected device, platform, or application. For example, a human resources system might run on an Oracle platform while a payroll system might run on a Sybase platform.

Those skilled in the art may use the present invention to store common sensitive data on the secure server 204 so that it is centrally located and easily accessed by all applications as regulations and business practices change. The present invention adds cross-platform interoperability and flexibility to existing legacy and enterprise systems for the data that is currently at most risk to process change.

Those skilled in the art may also use the present invention to centralize sensitive, critical, or complex data that is likely to be affected by new regulations. For example, a Federal Trade Commission's Data Disposal Rule permits individuals to contact companies that have collected their credit data. Individuals may request that these companies permanently dispose of this data, which could be stored in multiple servers running multiple applications. The present invention gives companies new tools to centrally store and manage this type of data so that it can be, in this example, easily located and disposed of.

Authentication Layer—Who Has Access

The authentication layer 214 validates all access to plug-ins 230 and secure storage 210, including all requests from content manager 208. One preferred embodiment is storing the authentication rules in authentication table 238 that include:

Who has access, including authorized user names, types of authentication permitted, authentication values such as passwords and biometric data.

What applications and systems each user may access.

When each user may access, including hours of the day and days of the week, as well as how often each user must re-authenticate.

Where each user must access from, such as VPN addresses or specific device identifiers.

Why each user has access so that suspicious behavior can be examined.

What action must be taken when authentication fails. This can be as simple as logging the request and suggesting the user enter a new password to notifying a supervisor and downloading code so the client's content manager 208 can destroy the client storage 206 and client hardware.

Figure 7:
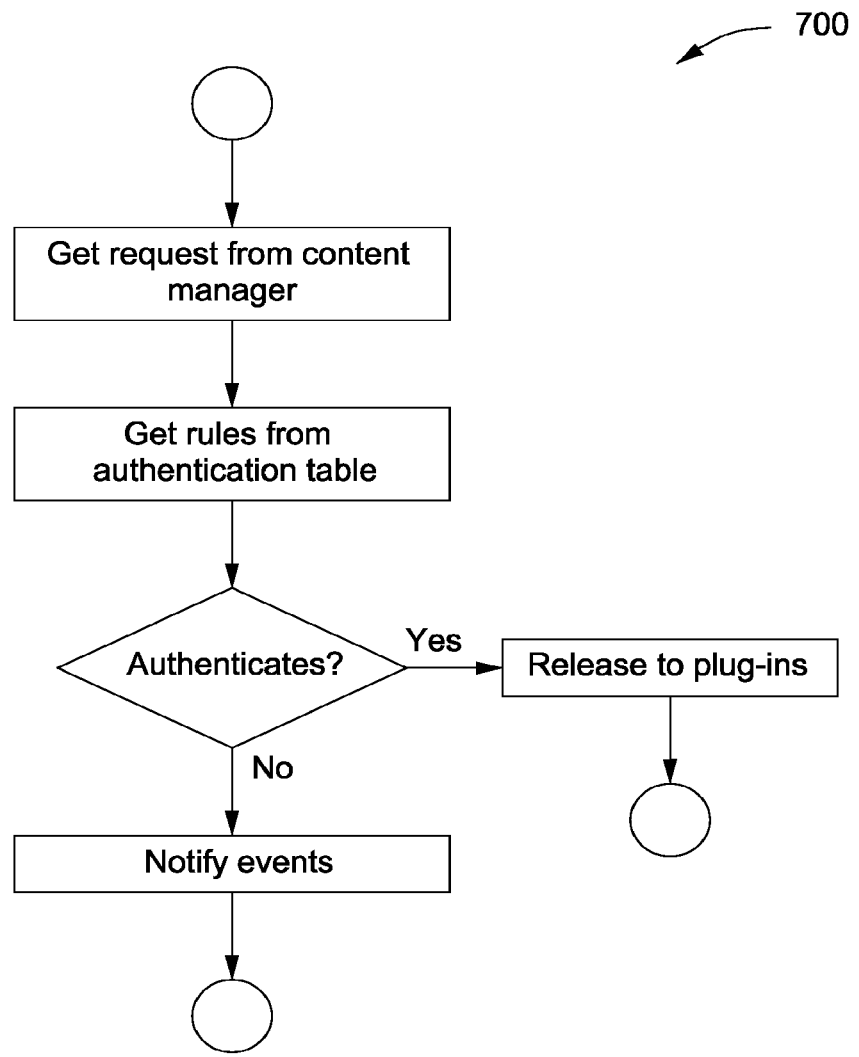
FIG. 7 illustrates the authentication process in accordance with one embodiment of the present invention.

In the preferred embodiment, the authentication rules 228 are dependant on the user, how much protection is required by the application 222, and the type of sensitive data that is in secure storage 210. Weak authentication could be a simple password entered on a laptop client running the application 222. Strong authentication could be a biometric fingerprint device on a specific laptop that can only be used at certain times of the day, and only while the user's finger remains on the biometric device. Referring to FIG. 7, authentication is dependant on rules defined in the authentication table 238.

Those skilled in the art may use the present invention to also authenticate with other methods. Authentication could be, for example, by system, table, and/or field name. For example, a global rule for all Social Security Number fields can be set, irrespective of who is accessing the secure server 204.

Figure 8:
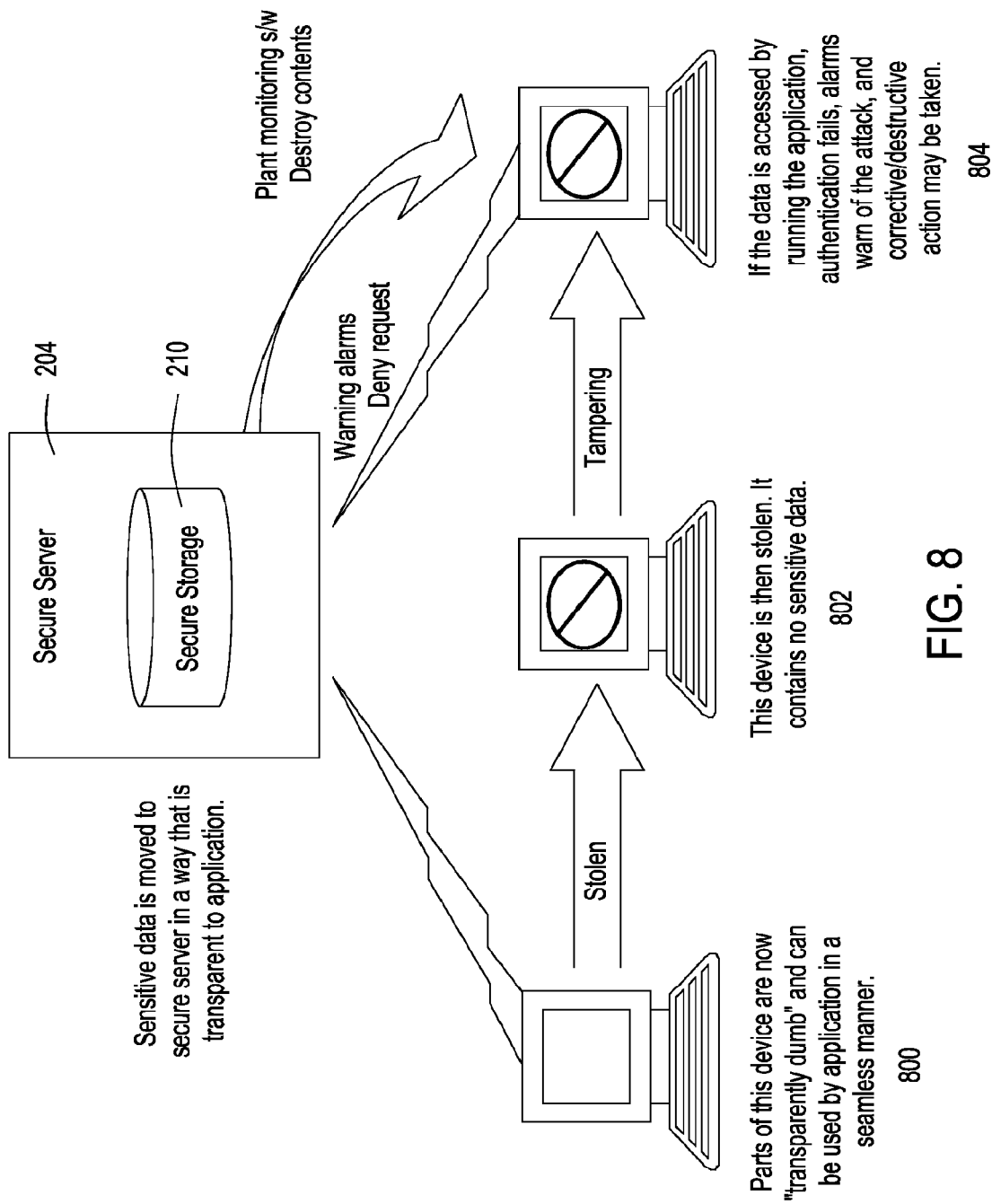
FIG. 8 illustrates how stolen data or a stolen device does not contain any sensitive data in accordance with one embodiment of the present invention.

Referring to FIG. 8, stolen data or a stolen device does not contain any sensitive data when the present invention is used because the sensitive data has been moved to the secure server 204 in a way that is transparent to the application 222. The only way to retrieve the sensitive data is to run the application 222 and content manager 208. As a result, parts of the device are now "transparently dumb" and can be used by the application 222 in a seamless manner 800. If the device has been reported as stolen 802, or if authentication fails 804, then appropriate action is taken by events manager 232, which could include warning alarms, denial of the request, and/or downloading code to the client content manager 208 that monitors behavior and/or destroys data and/or the client hardware.

Figure 9:
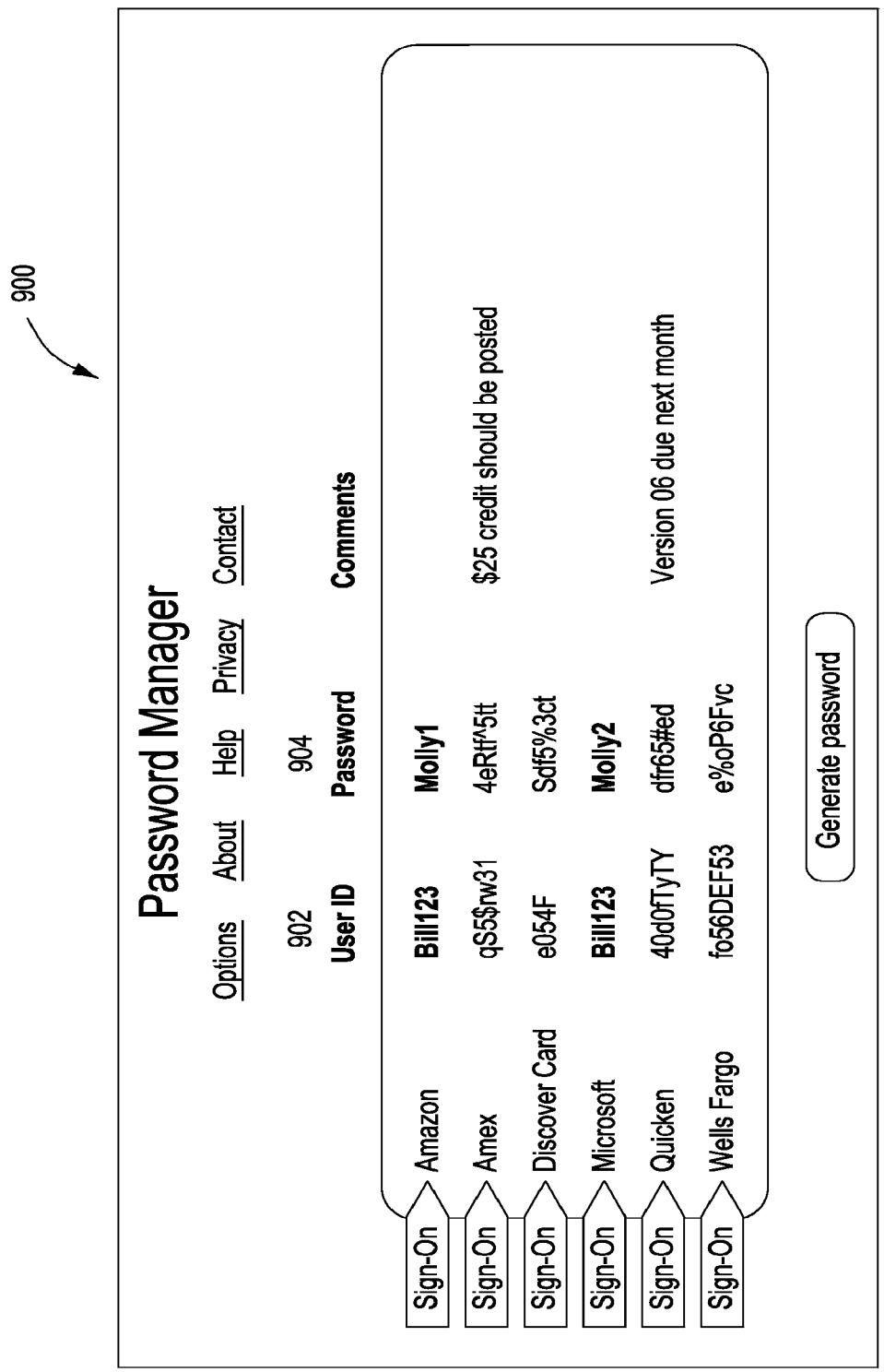
FIG. 9 illustrates a Password Manager application in accordance with one embodiment of the present invention.

Another embodiment of the present invention extends current Web authentication systems. Referring to FIG. 9, a Password Manager application 900 collects and stores sensitive data (User ID 902, Password 904) in secure storage 210. Using strong authentication, such as with a biometric device, the Password Manager application 900 enables single-click sign-on to any Website. This is done by:

The user authenticating with Password Manager 900.
The Password Manager application 900 getting the User ID 902 and Password 904 from secure storage 210.
The Password Manager application 900 passing this to a browser application.
The browser application using this to sign-on to the desired Website.

Note that this Password Manager application 900 is an example of when archiving is not required on the secure server 204 because when a password changes the previous value is not required, so the new value may override the previous one.

Plug-Ins Layer

Figure 10:
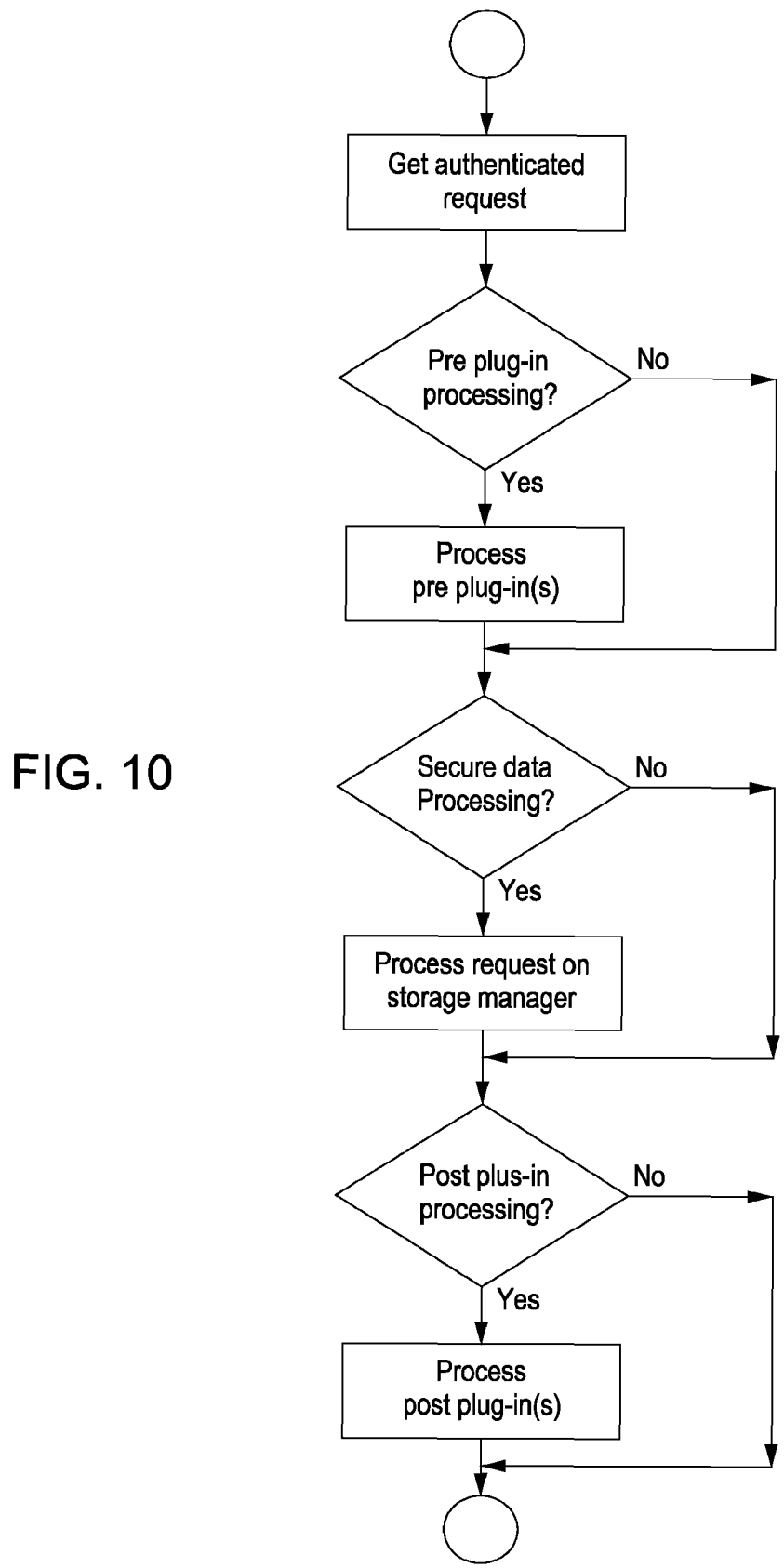
FIG. 10 illustrates how plug-ins are used to examine and control content manager requests in accordance with one embodiment of the invention.

Plug-ins 230 process authenticated requests from content manager 208. Referring to FIG. 10, plug-ins 230 are used to examine and control content manager 208 requests before and after storage manager 234 gets sensitive data from or puts sensitive data in secure storage 210.

Plug-ins 230 work with their own API's that permit any process or program to extend the capabilities of the present invention. For example, Sarbanes-Oxley compliance is so expensive that it can be measured as a percent of total revenue. Some of these costs involve auditing who has access to what sensitive data. In spite of these auditing controls, there is no audit or firewall that will prevent a trusted employee from copying sensitive data to, say, a flash drive for illegal purposes. The present invention ensures that the data copied from client storage 206 contains no sensitive data. Plug-ins 230 ensure that all access to the sensitive data in secure server 204 can be examined, denied, enhanced, and/or logged in an audit trail as needed.

Plug-ins 230 work in different ways. Pre processing plug-ins examine requests before sensitive data is got from or put in secure storage 210. Control may or may not then be passed to the data layer. Post processing plug-ins examine the results after data has been got from or put in secure storage 210. Plug-ins 230 may store temporary or permanent instructions or values in plug-in table 244 or external tables as needed. Plug-ins 230 may deny, enhance, or act on any request.

Plug-ins 230 embodiments may be used to:
Look for suspicious behavior.
Count how sensitive data is accessed for billing purposes.
Ensure that outsourced sensitive data is properly used.
Guard against triangulation or inference attacks.
Integrate with other third party access control systems to enhance the authentication process in the present invention.
Log all access to specific sensitive data, such as a trade secret or a SSN.
Assure compliance with regulations, such as SOX, HIPAA, GLB, the EU Data Directive, Homeland Security, SB-1386, or any new regulation.
Monitor access to dummy data intentionally stored where it can be stolen. This enables a new type of "honey pot" that could yield valuable information about how stolen data is traded or sold. The plug-in 230 could instruct the requesting content manager 208 to send additional data about the client 202 for law enforcement officers.
Send a client's content manager 208 additional code for version control, feature update, forensic analysis, behavioral tracking, data destruction, hardware destruction, or any other purpose.
Send any other process to the content manager 208 that is required by a specific industry expert, revenue model, or other custom purpose. Note that this can be sent at any time, thus allowing the rules for access to client storage 206 to be modified retroactively. The Holy Grail of security, as defined by the Center of Democracy and Technology, is the ability to control sensitive data after it has been released to others. Plug-ins 230 enable this.
Generate random numbers and characters to provide content managers 208 with unique pointers that replace sensitive data in secure storage 210. This is an example of a plug-in 230 that does not call storage manager 234, but returns a random pointer to content manager 208.
Many firms use outsourcing as a way to manage increasing costs. For example, inventory control has traditionally been considered a core capability, but increasing services from firms like UPS and FedEx permit freight companies to manage a firm's inventory. In the same way, the increasing costs and skill required to manage sensitive data makes this process an outsourcing candidate. Plug-ins 230 provide the framework for trusted firms to manage sensitive data as well as many of the applications 222 that access this sensitive data. For example, an auditing firm could process a client's human resources while providing assurances that Sarbanes-Oxley, HIPAA, GLB, and all other regulations are being met. This provides new revenue models for, say, auditing firms while permitting their client firms to reduce liabilities, save money, and focus on their core capabilities.
Another plug-in 230 example is for firms that manage sensitive data that must be sent overseas for outsourced applications. This permits outsourcing to continue without the need to send large amounts of sensitive data overseas.

Another is for a firm that uses the present invention to store critical encryption keys or other critical components of a client application 222. In this embodiment, plug-ins 230 could use secure server 204 or its own storage to archive these keys and/or critical components. This value-added service could prevent a catastrophic loss of data if the encryption keys or critical data is lost by a firm.

Another is logging critical encryption keys for safe storage.

At regular intervals set by a system administrator, a plug-in 230 can contact one or more client devices 202 to ensure that they are still connected to the secure server 204. If they are not, then the plug-in 230 and/or events manager 232 can take the appropriate action. For example, access can be disallowed and a supervisor can be notified. In another preferred embodiment, the content manager 208 can notify a plug-in 230 at regular intervals.

Plug-ins 230 turn the capabilities of the present invention into a flexible, open platform for many uses related to data security, tracking, revenue, theft, forensics, and resolution.

Data Layer—Getting Sensitive Data from the Secure Server

When application 222 gets records from client storage 206, it communicates with content manager 208 in a way that is transparent and seamless in most cases, thus requiring no program changes in application 222 (if changes are required, they are discussed in Enterprise System Upgrades).

Figure 11:
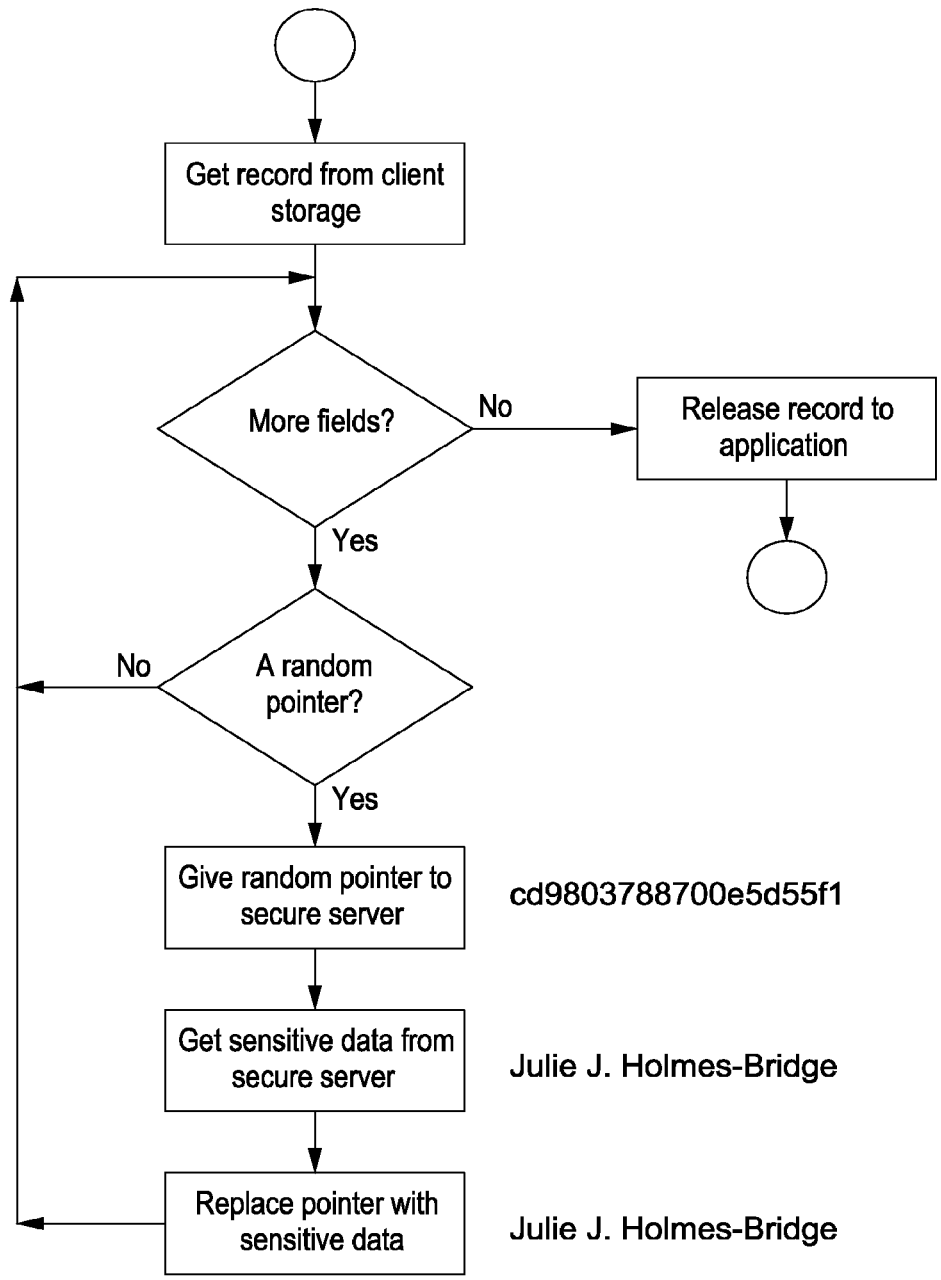
FIG. 11 illustrates how the content manager processes a request to get a record from client storage in accordance with one embodiment of the invention.

FIG. 11 describes one embodiment of how the content manager 208 processes a request to get a record from client storage 206. Each field is examined by content manager 208. If the field contains a random pointer, it is passed to the secure server 204 and, with correct authentication, gets sensitive data back that is then put back into the field. When all fields have been examined, the record is released to the application 222. Note that the record with sensitive data is not put in client storage 206.

Figure 12:
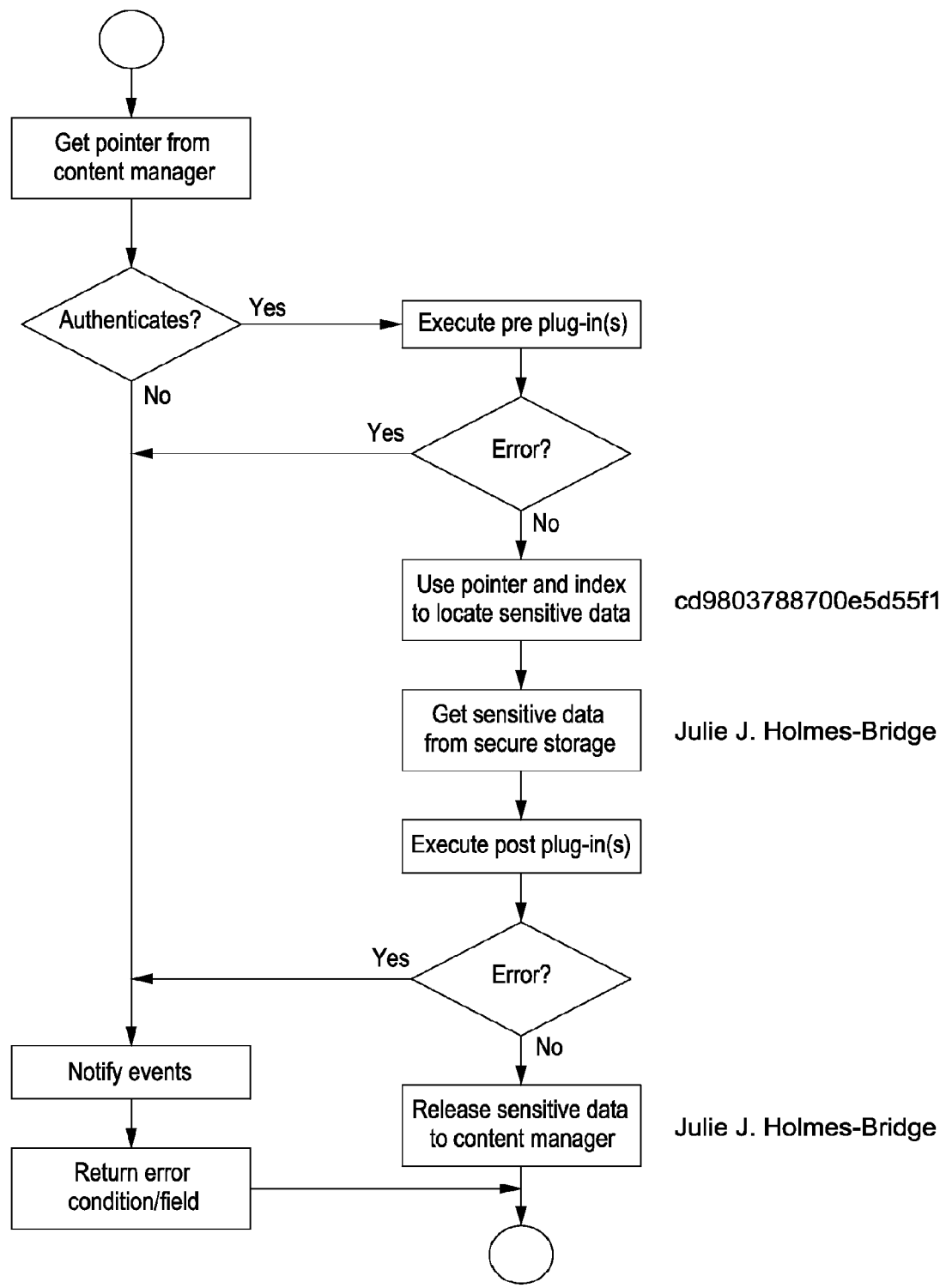
FIG. 12 illustrates how each content manager request to get sensitive data is processed on the secure server in accordance with one embodiment of the invention.

FIG. 12 illustrates how each content manager 208 request to get sensitive data is processed on the secure server 204. If the request does not authenticate, then the events manager 232 is notified so that the appropriate action(s) are be taken and/or error condition(s) set. Error values may be a blank value, an erroneous value, or any other value as defined by a system administrator.

If the request does authenticate, then one or more pre-processing plug-ins 230 may be executed, the storage manager 234 uses pointer and index to locate the sensitive data in secure storage 210, and one or more post-processing plus-ins 230 may be executed. If there are no error conditions from the plug-ins 230 or retrieval, the sensitive data is released to the content manager 208. In another preferred embodiment, multiple fields may be retrieved from secure server 204 at once rather than one at a time.

Data Layer—Putting Sensitive in the Secure Server

When the application 222 wants to put records in client storage 206, it communicates with content manager 208 in a way that is transparent and seamless, thus requiring no program changes in application 222 (if changes are required, they are discussed in Enterprise System Upgrades).

Figure 13:
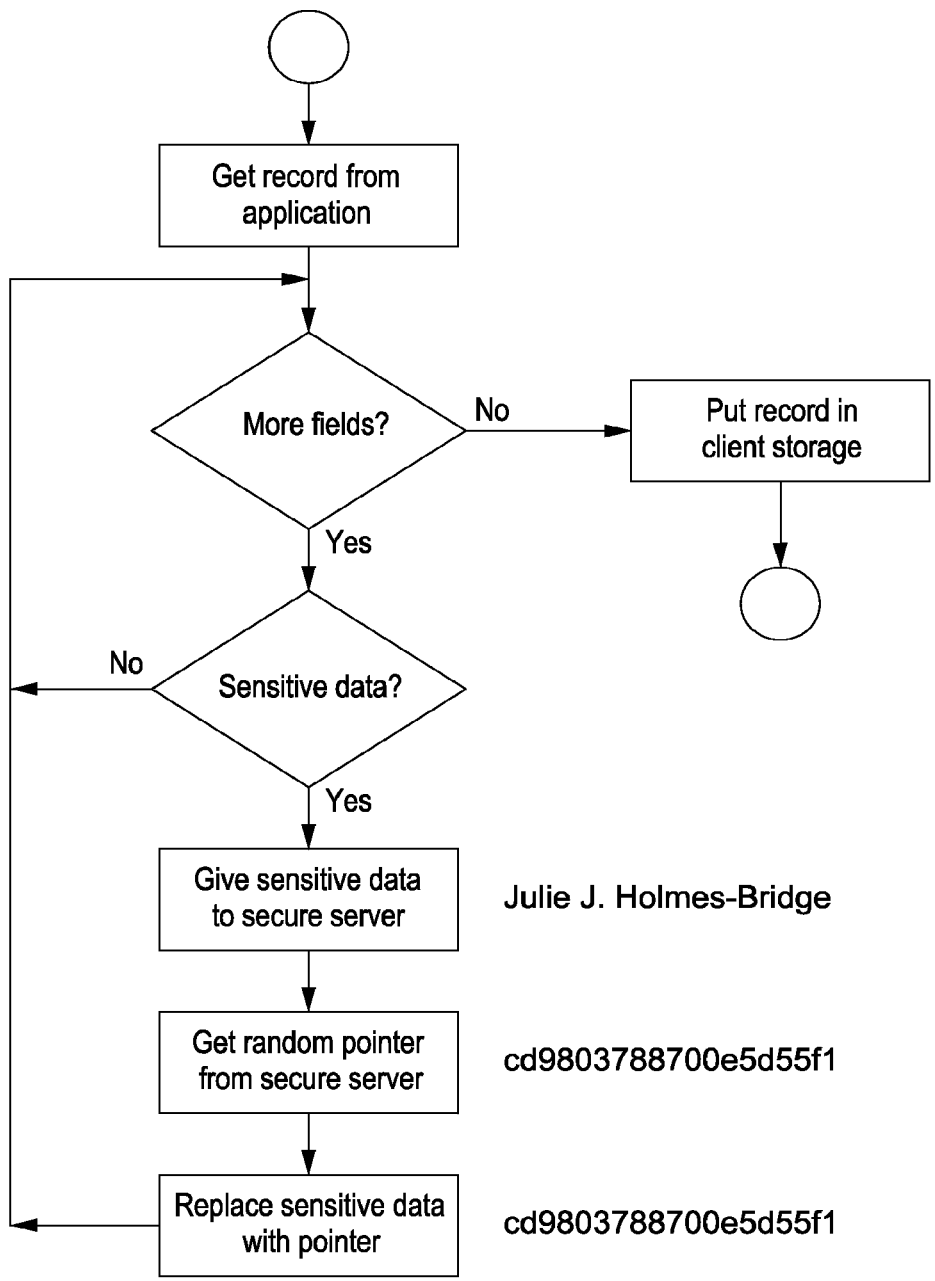
FIG. 13 illustrates how content manager processes a request to put a record in client storage in accordance with one embodiment of the invention.

FIG. 13 describes one embodiment of how content manager 208 processes a request to put a record in client storage 206. Each field is examined by content manager 208. If the field contains sensitive data, it is passed to the secure server 204 and, with correct authentication, receives a random pointer that replaces the sensitive data. When all fields have been examined, the record is put in client storage 206. Note that the sensitive data is not put in client storage 206.

Figure 14:
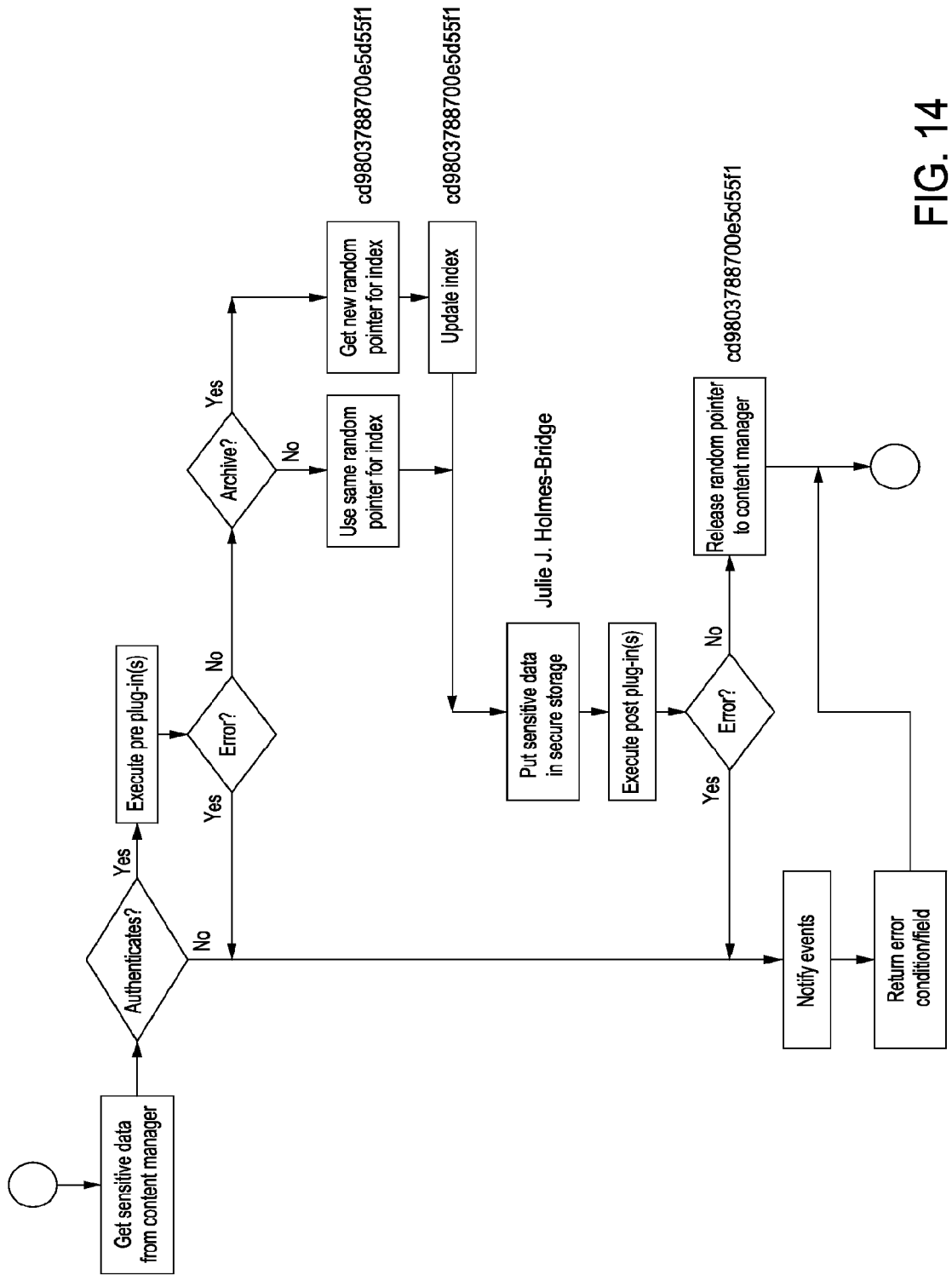
FIG. 14 illustrates how each content manager request to put sensitive data is processed on secure server in accordance with one embodiment of the invention.

FIG. 14 illustrates how each content manager 208 request to put sensitive data is processed on secure server 204. If the request does not authenticate, the events manager 232 is notified so that the appropriate action(s) are be taken and/or error condition(s) set. This error value may be a blank value, an erroneous value, or any other value as defined by a system administrator.

If the request does authenticate, then one or more pre-processing plug-ins 230 may be executed. The storage manager 234 determines the following: if automatic archiving is required, then a new random pointer is generated by a plug-in 230 and updated in index 246. If automatic archiving is not required, then the same random pointer is used. The sensitive data is put in secure storage 210. One or more post-processing plus-ins 230 may be executed, and the random pointer is returned to the content manger 208.

Applications that do not require archiving in secure storage 210 include Password Manager because old passwords are never needed. Most applications will require archiving because data may be shared, backed-up, or have multiple versions in use at the same time. In this case, each version of each table in client storage 206 must be able to retrieve its original sensitive data from secure server 204. In another preferred embodiment, multiple fields may be put in secure server 204 at once rather than one at a time.

Storage Manager

Figure 15:
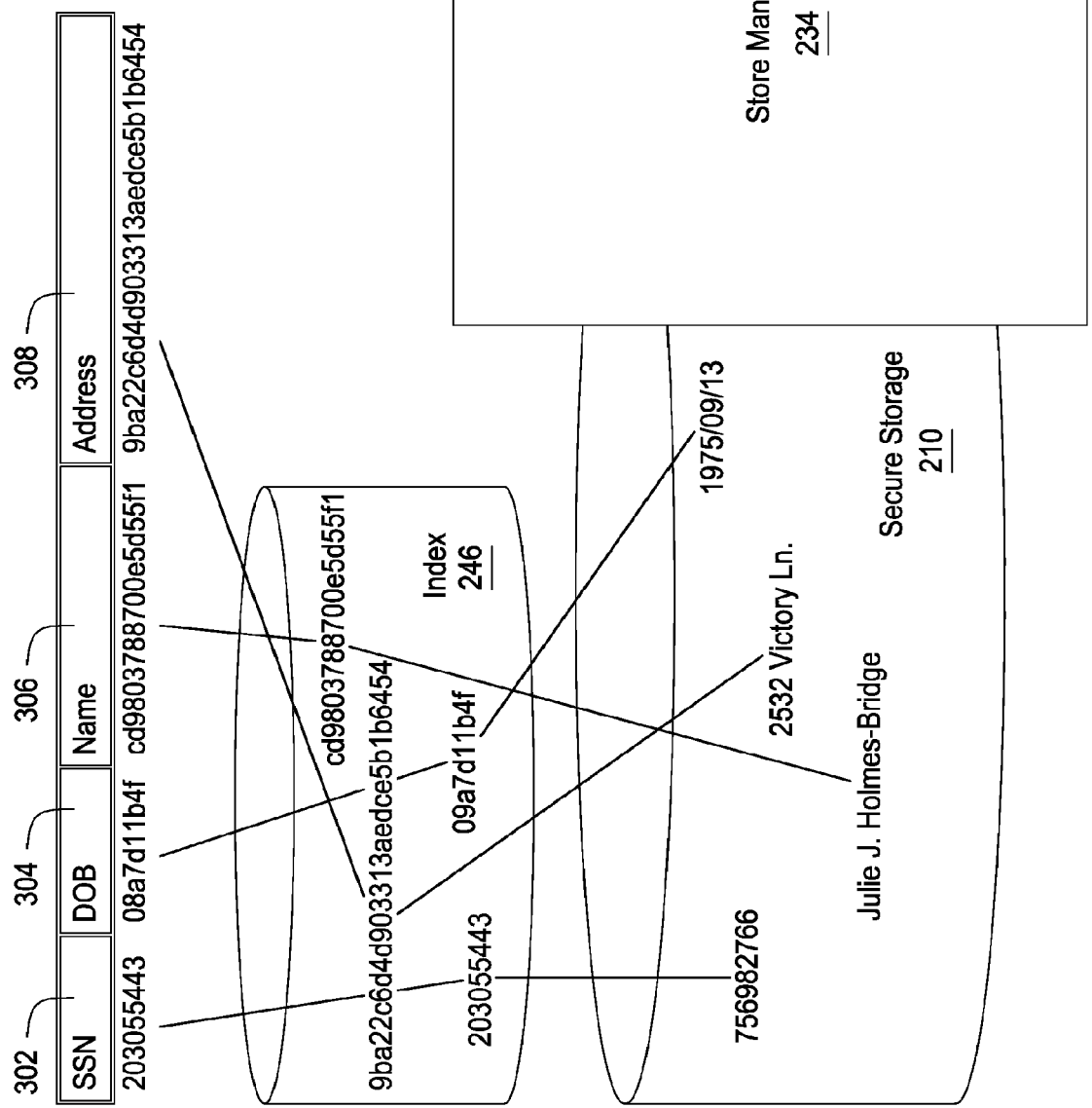
FIG. 15 illustrates how the storage manager uses random pointer and index to locate the sensitive data in secure storage in accordance with one embodiment of the invention.

Storage manager 234 gets sensitive data from and puts sensitive data in secure storage 210. Storage manager 234 uses index 246 to rapidly determine the correct location in secure storage 210. Index 246 may include any method, including indexing or hashing. For example, FIG. 15 illustrates how the storage manager 234 uses random pointer and index 246 to locate the sensitive data in secure storage 210. Each item, such as SSN 302, DOB 304, Name 306, and Address 308, is put in a separate location in secure server 204. This ensures that triangulation and inference attacks cannot glean sensitive data from the relationship of different values.

For example, some statisticians have shown that knowing a person's date of birth and five digit zip code uniquely identifies them over 90% of the time. The present invention prevents this because date of birth and zip code are not put in index 246 or secure storage 210 in a way that can be associated.

Index

Figure 16:
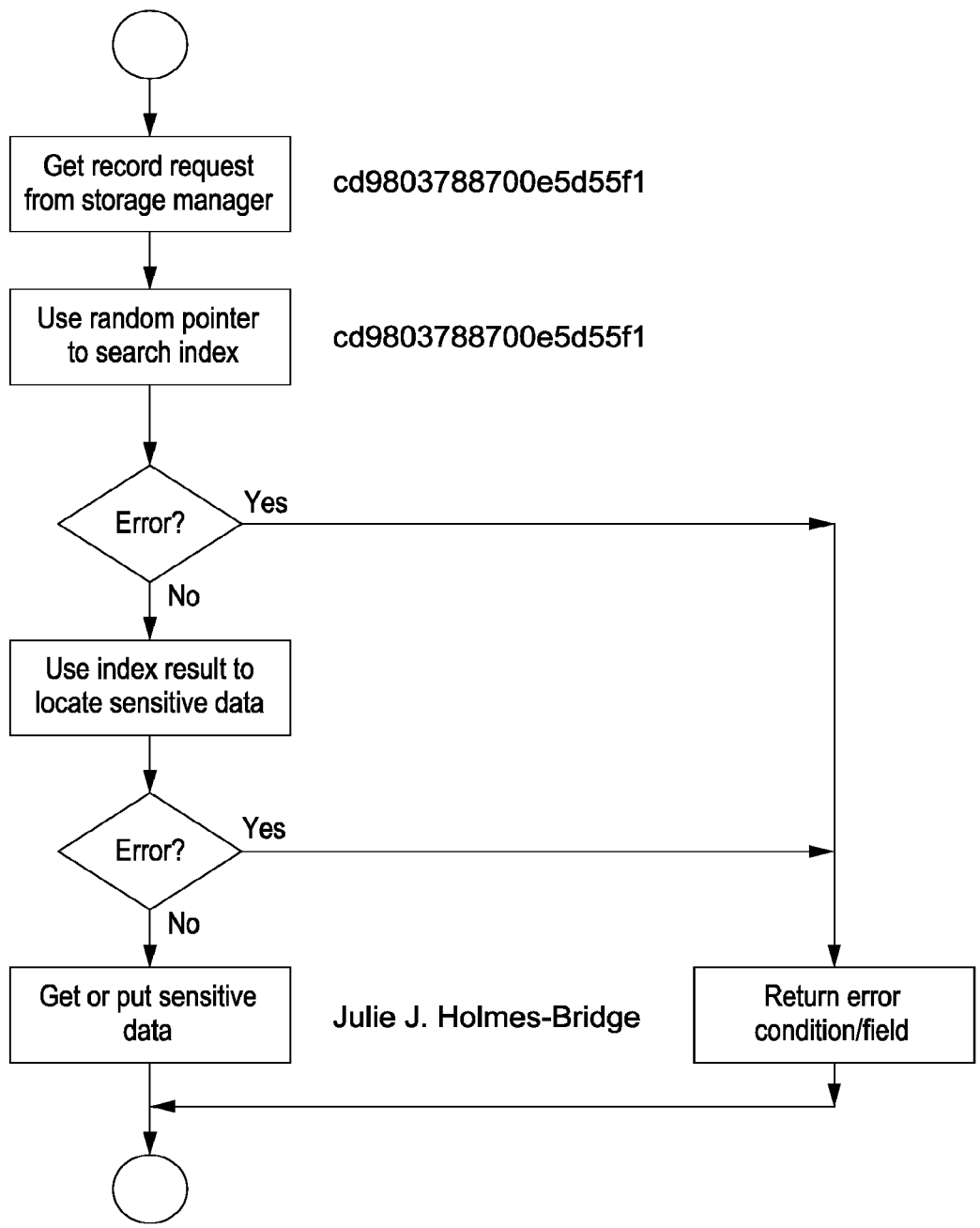
FIG. 16 illustrates how the index takes a random pointer from storage manager and uses it to locate an address in index in accordance with one embodiment of the invention.

FIG. 16 illustrates how the index 246 takes a random pointer from storage manager 234 and uses it to locate an address in index 246. This address contains sensitive data in secure storage 210. In the preferred embodiment, index 246 is any indexing method that permits using the random pointer to rapidly access the address in secure storage 210 of the desired sensitive data.

Index 246 may be stored across multiple physical servers to reduce the chance that a single trusted person would have access to pointers that could reconstruct an entire record from client storage 206.

Secure Storage

Referring back to FIG. 2, index 246 and secure storage 210 are shown as single files. Other preferred embodiments may include a combination of the following:

Mirrored files in separate physical servers. This protects against hardware, power, or environmental failure.

Index 246 or sensitive data fields in secure storage being stored randomly on different physical servers. This protects against a single trusted person having access to all of the index 246 or sensitive data in secure storage 210.

Sensitive data fields being split so that that, say, the first 4 bits of each byte is stored in one physical server and the other 4 bits of each byte stored on another physical server. This protects against a single trusted person having access to a sensitive data field.

Encrypting the data on the client side and on the server side with different keys that are never exchanged. The server keys would be stored in a different location from the data.

Another embodiment to obfuscate sensitive data fields using bit separation to split the data into separate components is described:

Generate n−1 bit strings, where n is less than the number of bits in the original data, to separate the data into n separate pieces. For example using the original bit string 1011, separating into 3 parts would require 2 mask bit strings (1010, 0110).

To get string part 1 AND the original bit string with the first mask string (1011 AND 1010=1010).

Next, calculate the remainder by XORing the original bit string with string part 1 (1011 XOR 1010=0001).

Next take the remainder and AND that with string part 2 (0001 AND 0110=0000).

Then calculate the reminder by XORing the previous reminder with string part 2 (0000 XOR 0001) to product the final string part.

This result in 3 string parts (1010, 0000, 0001) which can then be XORed together in any order to reproduce the original data. Also any string part that is all 0's can be discarded to save space.

Those skilled in the art will use index 246 and secure storage 210 to design new ways to ensure that sensitive data is always stored in a way that is safe from hardware, power, environmental, or intentional human failures.

Events Manager

Figure 17:
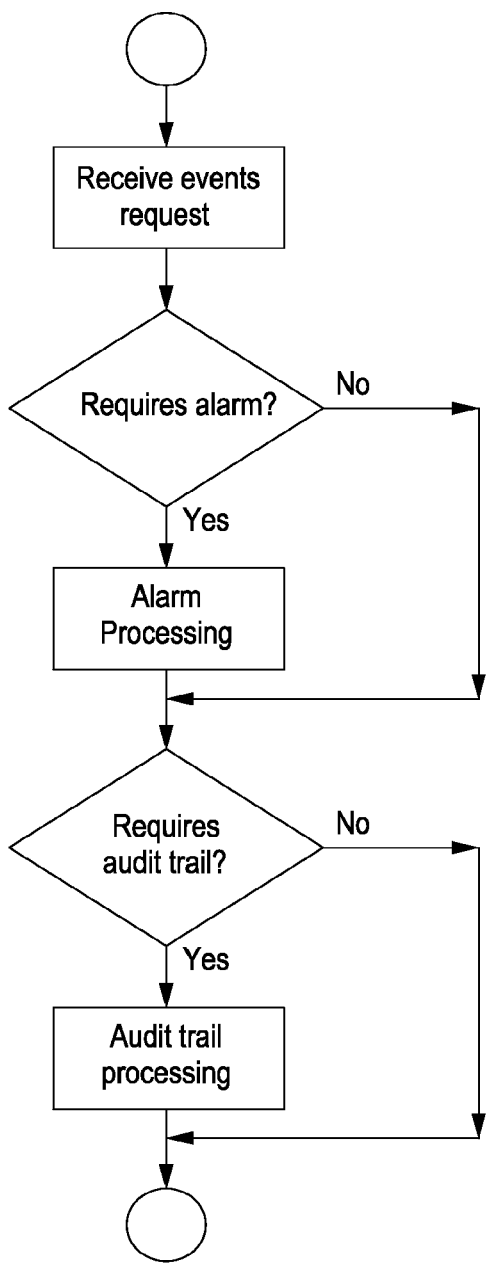
FIG. 17 illustrates two event types received or detected by the events manager in accordance with one embodiment of the invention.

The events manager 232 may be activated by authentication 228, plug-in 230, and/or storage manager 234 requests. In the preferred embodiment, two event types are shown in FIG. 17. The first is an alarm 240 that could include calling a manager on a cell phone and sending a message to authentication rules to deactivate access for all applications on a particular laptop client. The second is an audit trail 242 that could include sensitive data accessed by all laptops so that if one is stolen, a finite number of customers can be notified under California's SB-1386 notification regulation. Those skilled in the art may add other event types of events to the present invention.

Digital Rights Management (DRM)

Figure 18:
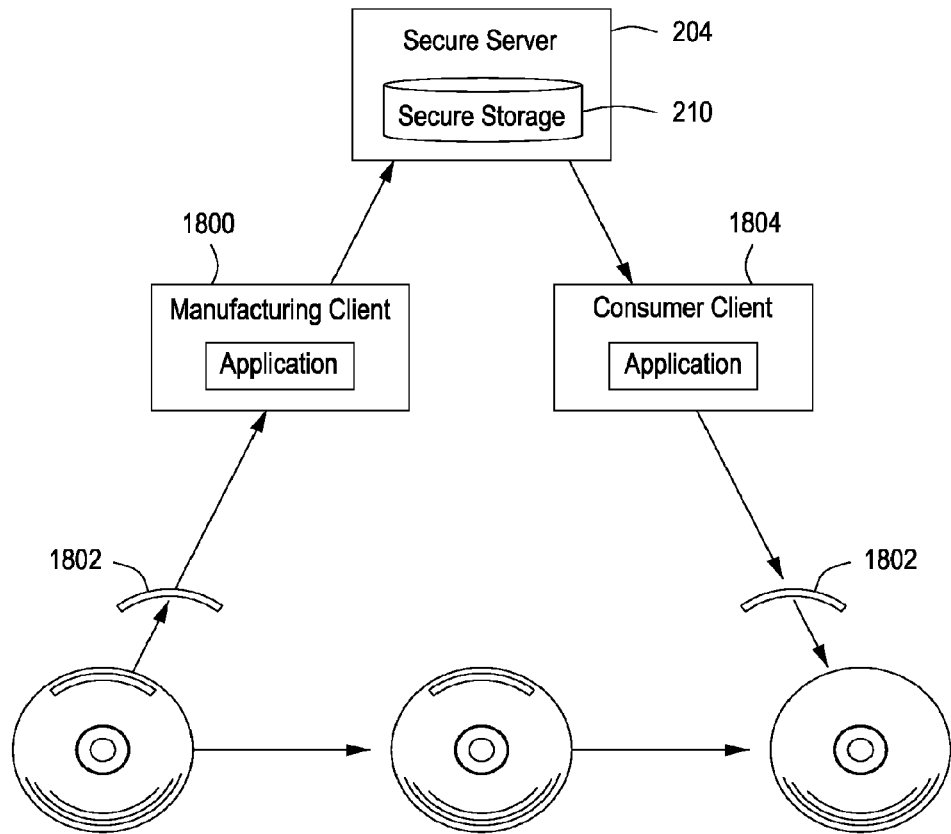
FIG. 18 illustrates how the present invention can be used by a manufacturing client to remove critical components of, say, a DVD so that the DVD may be previewed but not played in full.

Another embodiment of present invention is protecting different types of sensitive data in a way that represents a new type of digital rights management. FIG. 18 refers to one embodiment where a manufacturing client 1800 removes critical components 1802 of, say, a DVD so that the DVD may be previewed but not played in full. These critical components 1802 are put in secure storage 210 under the full protection of the present invention. The DVD with the critical components 1802 removed can then be distributed as a sample, and any number of copies can be made by interested parties.

Anyone can load the DVD and can preview the contents of the DVD, but cannot play the entire DVD because the critical components 1802 are missing. With proper authentication from the consumer's client 1804, the secure server 204 can provide the missing critical components 1802 to the original DVD content. The critical components 1802 are seamlessly merged back by content manager 208 so that the original content can be viewed by the consumer, but not in a way that the data from the DVD and critical components 1802 can ever be stored together. Without proper authentication, the secure server 204 can take any action as shown in FIG. 8.

Other embodiments include always authenticating with no rules and using the present invention to count the number of times a DVD is played, what parts of the DVD are the most popular, what other digital content is known to content manager 208 for this individual, and so on. Still other embodiments include DRM protection for different geographical regions that the digital content is sold in, different industries, different media types, or any other market segment. Moreover, other embodiments include different types of digital content, including:

PDF newsletters that are always up-to-date.

Catalogues that are personalized to the color, style, size, shipping preferences, and loyalty program of each individual consumer.

Software, hardware devices, and games that cannot be used unless a paying customer has authenticated.

Protecting any other type of digital content, including phone numbers, games, movies, music, pictures, videos, email, program code, art, photos, passwords, news, IP, documents, DVDs, CDs, and patents.

Those skilled in the art will be able to make the present invention assure that revenue models are tied to people who authenticate before the critical components 1802 are released from secure storage 210. These revenue models could, for example, include every time a DVD is played, validating a membership or subscription, validating a software key, charging for the features used in software and/or hardware. The present invention can be used to retroactively enable new revenue models even after, say, the DVD with critical components removed has been widely distributed. The present invention gives the owner of the original content control for payment, auditing, destruction, or any other purpose.

Forensic Analysis

Another embodiment of present invention is tracking data to enable a unique type of forensic analysis. Current forensic analysis requires access to disk files, tapes, CDs, DVDs, flash drives, memory, and other types of digital storage media.

Figure 19:
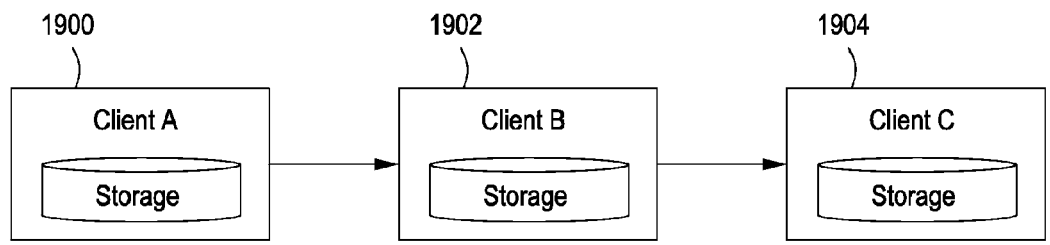
FIG. 19 illustrates tracking data to enable a unique type of forensic analysis in accordance with the present invention.

Referring to FIG. 19, digital content, such as an email message, can be created on client A 1900, sent to client B 1902, and then forwarded to client C 1904. In order to determine that the message is on client C 1904, the forensics analyst must have access to all three clients, and their contents must have been preserved. This is also problematic because the "trail" of messages cannot be broken. This is further problematic because the message can be transferred from one client to another in a manner that cannot be analyzed, such as by CD. This is even further problematic because multiple copies of the message could have been made, and may be in clients that are unknown, inaccessible, destroyed, or even overseas.

The present invention solves these problems because the trail of data is not required in order to perform forensics analysis. Referring to FIG. 8, a client 202 is stolen and can be moved to any location. Copies of client storage 206 can be made and again moved to any location. Any number of stolen data can end up on any number of clients 202 in any number of locations or countries.

As shown in FIG. 2, the present invention protects digital content not by how it got there but by the need to authenticate with the secure server 204 before sensitive data can be used by the client 202. The present invention provides a way to ensure that digital content is:

Protected, no matter where it is located or how it got there.

Paid for, as defined by plug-ins 230.

Kept up-to-date or changed, as defined by the plug-ins 230 and sensitive data being returned.

Monitored, as defined by plug-ins 230.

Destroyed, as defined by plug-ins 230. This could also include software commands to destroy certain hardware components in the client 202.

Able to have new processes retroactively deployed for future unknown threats, opportunities, and requirements, as defined by plug-ins 230.

Referring to FIG. 4, one or more forensics processes may be set for any field in client storage 206 that requires processing by secure server 204. This field could be just a dummy tag used for tracking purposes only. One embodiment of a forensics process is a plug-in that puts sensitive data with a unique time/date/user stamp in secure storage for later forensic analysis. Referring to FIG. 8, this can use an unauthorized attempt to determine what copy of the client data was stolen, when it was created, and who was responsible for it. The present invention gives forensics analysts new, simplified tools to track, interpret, monitor, and destroy sensitive data and client hardware that they are stored on.

Addition Client Control

Those skilled in the art can use the present invention in general and content manager 208 in particular to seamlessly add functionality to any application 222. This may include the protection, monitoring, controlling, payment, or destruction of sensitive data or just regular data.

European Data Directive Compliance

Many state, federal, and international regulations are following the lead of the European Data Directive. For example, California's SB-1386 was based on the European model that people should be notified if their personal data is put at risk. One of the most stringent requirements of the EU Directive is that personal data cannot move from one country to any another unless the receiving country complies with the EU Directive. This has created problems for many EU firms. For example, firms in England cannot send certain data to its own branch offices in countries like South Africa because the latter is not EU Directive compliant.

Figure 20:
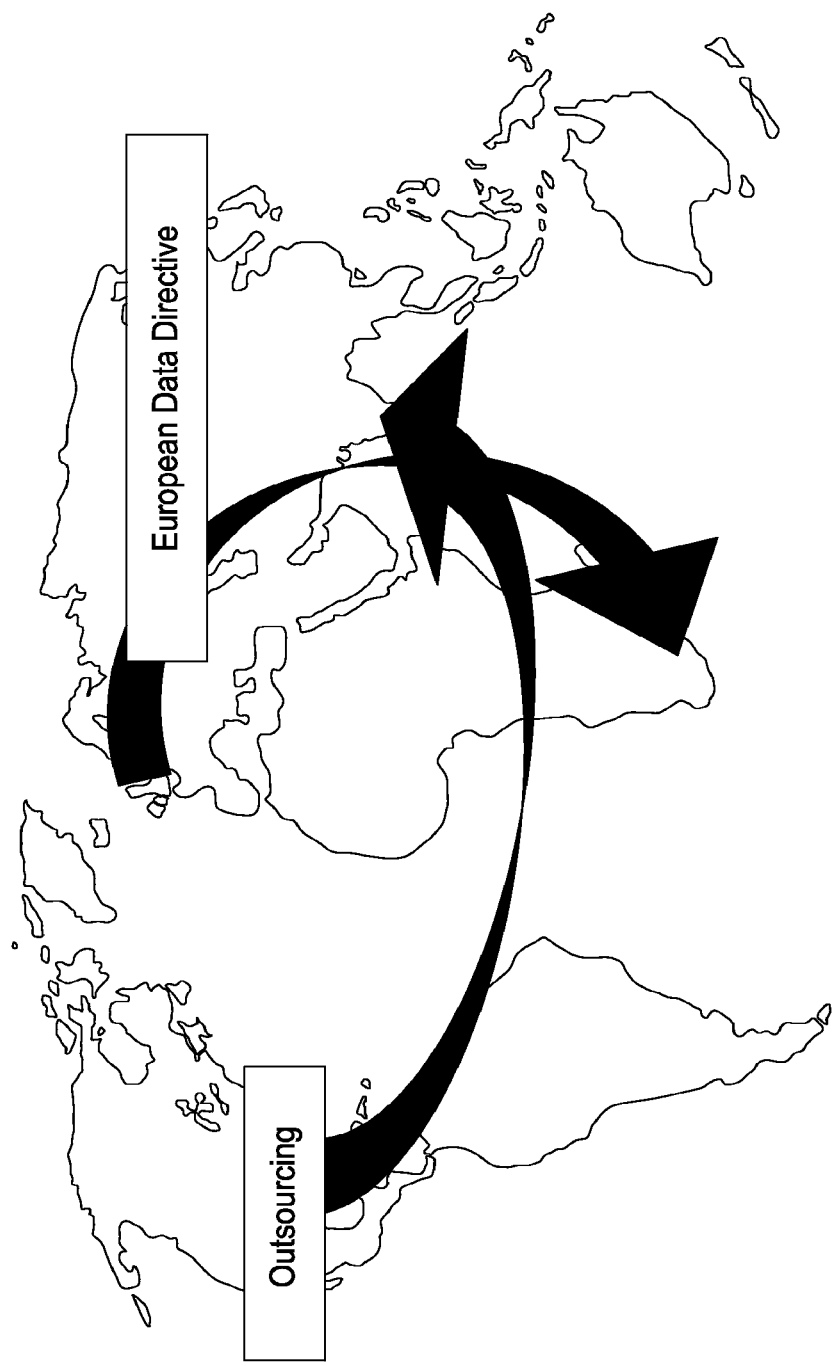
FIG. 20 illustrates how the compliance problems with governmental regulations and how outsourcing problems are solved in accordance with the present invention.

Referring to FIG. 20, the present invention solves this problem because sensitive or personal data is stored in a secure server 204 in England and never moves. Client devices, client storage 206, and client applications 222 are all free to move from business to business and from country to country because none contain sensitive or personal data.

If state or federal laws are passed that restrict the movement of sensitive or personal data, the present invention will provide an immediate solution reduce implementation and compliance costs. The present invention helps firms remain nimble in an increasingly costly and uncertain regulatory environment. The present invention provides a framework for protecting sensitive data for outsourcing to local companies and to overseas countries such as India.

An Enterprise Database Example

Referring to FIG. 3, enterprise database applications access tables in storage that contain sensitive data. A typical screen 2100 that accesses this data can be seen in FIG. 21. In the preferred embodiment, a database administrator creates a new table in client storage 206 or secure server 204 that contains information similar to the items shown in FIG. 4. This new table defines the fields in a system that needs protection. The database administrator then applies one or more triggers to tables or fields that need protection, and these triggers read the new table with the defined values. When the table in client storage 206 containing sensitive data has been converted, its resulting contents in client storage 206 can be seen in FIG. 5.

Referring to FIG. 22, application 2200 running on the left without authentication from secure server 204 returns the random pointers from client storage 206 that contain no sensitive data and cannot be cracked or unencrypted. However, application 2202 running on the right with authentication to and from secure server 204 returns sensitive data that is identical to FIG. 21. The present invention protects sensitive data in a way that is transparent and seamless to the enterprise database applications.

An Excel Example

The present invention can be embedded into any application 222. Another preferred embodiment is protecting sensitive data in Microsoft® Excel® files. Excel® is the most widely-used program to store and manage sensitive data. Yet the current ways to protect Excel® files are inadequate because they rely on passwords that can be cracked and encryption that can be complex to use. The present invention removes sensitive data from client storage 206 and puts it in secure servers 204 in a way that the sensitive data cannot be accessed without proper authentication.

One preferred embodiment is defining an entire Excel® file as sensitive data. The only way to access any data in this Excel® file when the client 202 is not connected to the secure server 204 is with client caching 224, which may reduce the overall security of the present invention.

Another embodiment is defining only the data in the Excel file that is sensitive. Referring to FIG. 23, Name 2300, Loan Number 2302, and SSN 2304 contain sensitive data while the rest of the Excel® file (credit score 2306, monthly payment 2308, overdue payments 2310, late charges 2312, other charges 2314 and total charges 2316) does not. A content manager 208 for Excel® has been installed on the client. In this embodiment, this is an Excel® plug-in 230 called "Theft-Proof Data" 2400 which can be seen in the command line.

Figure 24A:
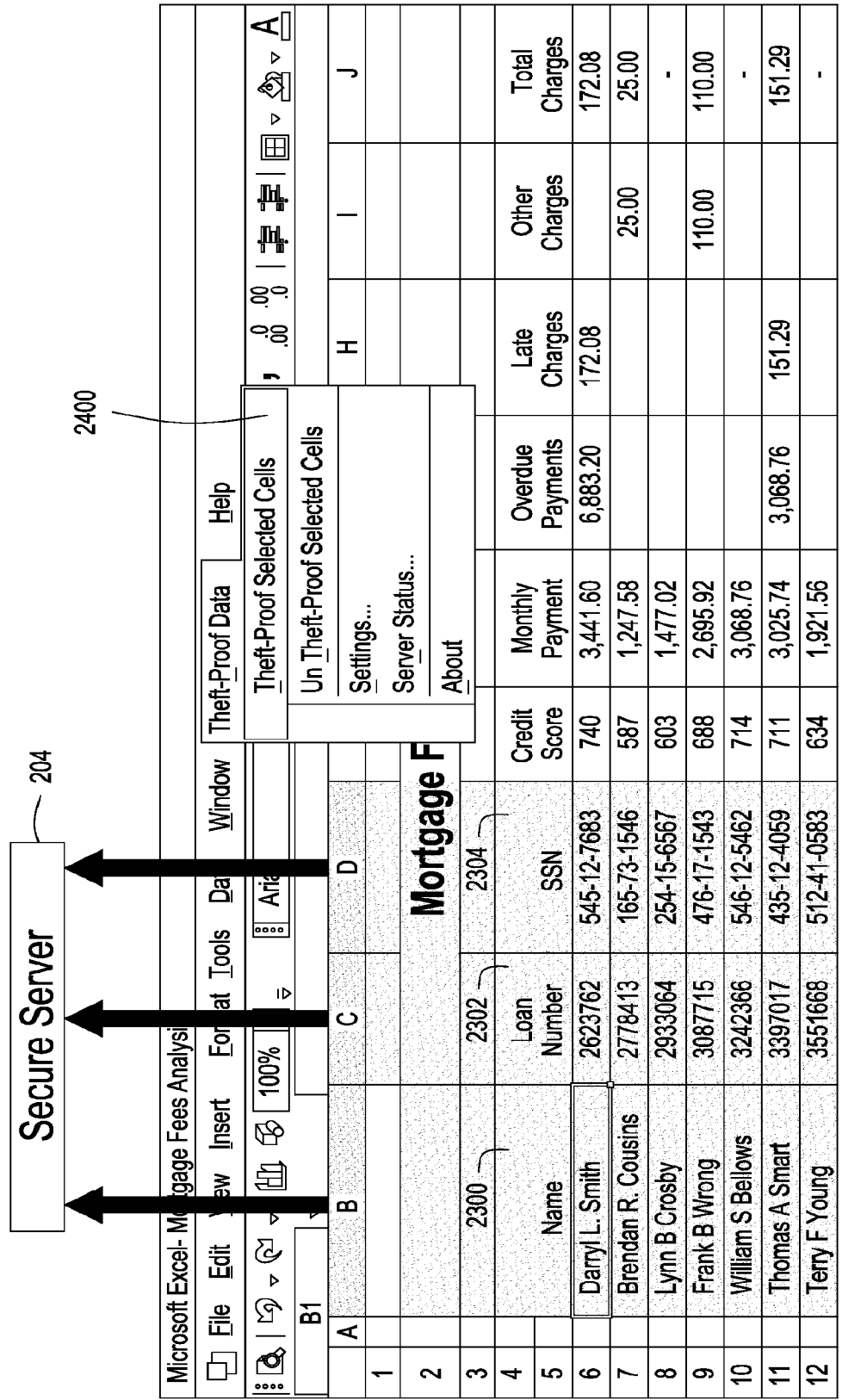

Referring to FIG. 24A, the columns containing Name 2300, Loan Number 2302, and SSN 2304 have been selected, the Excel® plug-in 2400 has been selected in the command line, and a command to "theft-proof" the selected cells has been clicked. Another preferred embodiment is right-clicking to "theft-proof" the selected cells. These perform the following:

- Referring to FIG. 2, client 202 communicates with secure server's 204 API 212, authentication 214, plug-ins 216, and data 218 layers.
- All sensitive Excel® cells are stored in secure storage 210.
- All sensitive Excel® cells are displayed with an additional attribute, such as the color red, as defined in settings. This helps the user see what cells are stored on client storage 206 and what cells are stored in secure storage 210.
- A plug-in 230 generates random pointers that content manager 208 places in the comments fields of the selected Excel® cells. These random pointers are later used by content manager 208 to access sensitive data in secure storage 210.

Whenever this Excel® file is saved or closed, all sensitive data is automatically and transparently stored in secure server 204 according to random pointers in cell comment fields. The sensitive data is blanked out before the Excel® file is stored in client storage 206.

When this Excel® file is opened, all sensitive data is automatically and transparently read from secure server 204. Whenever a theft-proof cell is added, changed, deleted, or the theft-proof attribute is added or removed from a cell, the content manager 208 Excel® plug-in makes the corresponding change in secure server 204. In this embodiment, all data stored in secure storage 210 has auto version control turned on so that different copies of this Excel® file remain synchronized with secure server 204. Opening this Excel® file on any device with proper authentication automatically synchronizes sensitive data again in a way that is automatic and transparent to Excel®, but in a way that does not store the sensitive data on the client.

Referring to FIG. 8, if the Excel® file is stolen or tampered with by accessing secure server 204 without proper authentication, the blank cells stored in client storage 206 are shown and not the sensitive cells stored in secure storage 210, as shown in to FIG. 24B. The pointers stored in comments are random data that do not contain sensitive data.

Another preferred embodiment has a central system administrator controlling which rows, columns, and/or cells are to be protected. Ways to do this include having rules embedded in the Excel plug-in or in Excel® files with predefined rows, columns, and/or cells.

Another preferred embodiment is having the plug-in examine the content of values entered into cells and then determining if the cell contains information that should be protected. This embodiment uses a table with different mask values to determine the likely value type:

| Mask Value | Likely Value Type |
|---|---|
| nnn nnn-nnn | Phone number |
| (nnn) nnn-nnn | |
| nnn nn nnnn | Social Security Number |
| free-formatted with 2 or 3 words | Name |
| free-formatted starting with a number | Address |
| nnnnn | Zip code |
| nnnnn-nnn | |

This determination can include examining surrounding cells. For example, if 80% of the values in a column look like a Name, then the entire column can be protected. This automatic determination has the advantage of enforcing protection, even for new Excel® files that a system administrator is unaware of. In another preferred embodiment, a central system administrator could set a default that all cells in a new file are protected until the file has been given proper security clearance.

Those skilled in the art may also use the present invention to protect sensitive data in other Microsoft® Office® products, including Word®, PowerPoint®, Access®, and Outlook®. For each, those skilled in the art will find places to store random pointers that are transparent to the application. These could include hidden text in Word® or PowerPoint®, an additional table in Access®, or an unused portion of an email header for Outlook®. Those skilled in the art may also use the present invention to protect sensitive information in other products, such Intuit's Quicken® and Adobe's Acrobat®.

Tracking Attempted Data Theft

In the preferred embodiment, when an Excel® file is protected for the first time, the Excel® plug-in 2400 stores a clear GIF file in a cell where it will automatically display when the file is opened. Each time the Excel® file is opened, but before the screen displays, the Excel® plug-in 2400 deletes this clear GIF file. Before the Excel® file is stored, this clear GIF file is put back for the next time it is opened.

In one preferred embodiment, the name of this clear GIF file includes the address of the events manager, the time, date, and person who authorized the last sensitive data to be accessed by this Excel® file. In another embodiment, the GIF file includes an address with the Excel® file name, time, date, and person who authorized the last sensitive data to be accessed by this Excel® file.

If the Excel® file is opened without Excel® plug-in 2400, the clear GIF is not deleted, so it attempts to load a remote file on the events manager 232. If a connection is made, the events manager 232 takes the appropriate action for when someone has opened an Excel® file without the Excel® plug-in 2400 because the potential theft of a protected Excel® file has been tracked. Those skilled in the art will develop similar ways to track the attempted theft of other types of data, such as Microsoft® Word® and PowerPoint®, and digital content, such as music and movies.

Figure 25A:
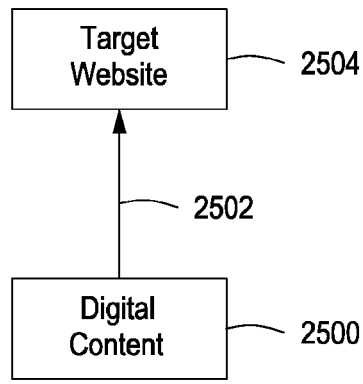
FIGS. 25A, 25B and 25C illustrate looking for one or more links in a digital content file being protected in accordance with the present invention.
Figure 25B:
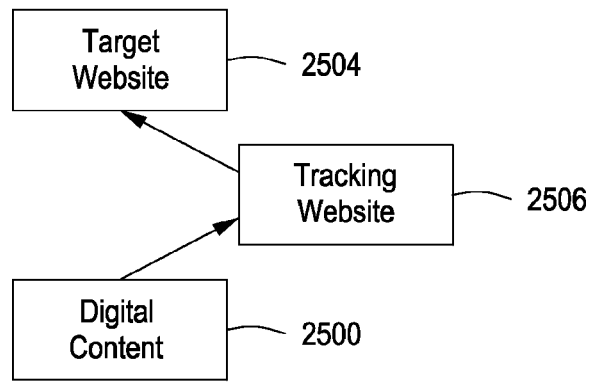

Referring to FIGS. 25A and 25B, another preferred embodiment is looking for one or more links in a digital content file 2500 being protected. If a link 2502 is present to a target Website 2504, it is changed to point to a tracking Website 2506 that records the event in the same manner as described for the clear GIF file. The tracking Website 2506 then redirects control to the target Website 2504.

Figure 25C:
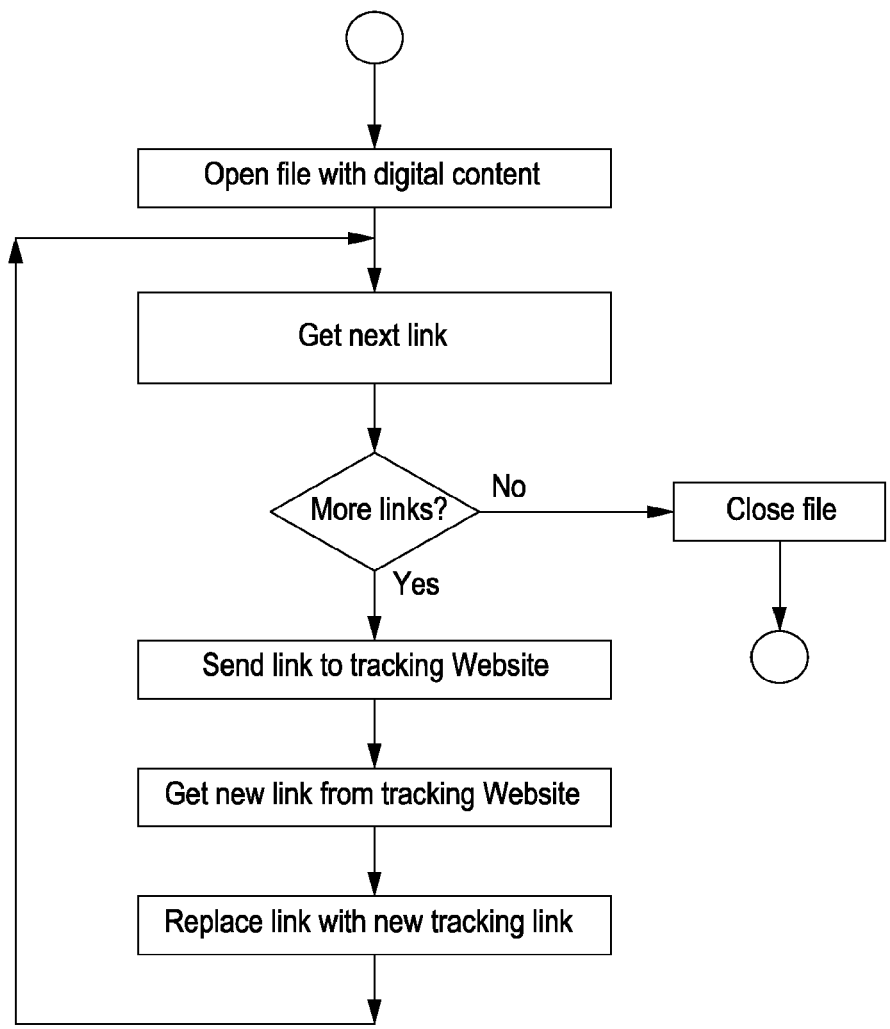

Referring to FIG. 25C, each link in the file is sent to a tracking Website 2506 that:

Creates a new link for the digital content file that points to the tracking Website 2506. In the preferred embodiment, this link includes the digital content file name, time, date, and person who authorized the last sensitive data to be accessed by the digital content file 2500. This is passed back to the digital content file 2500.

Creates a process in tracking Website 2506 that accepts and stores the link data from the digital content file 2500 before passing control to the target Website 2504.

This can be done for all links in the digital content file 2500 or for a specified maximum number of links. A clear GIF file can still be placed in the digital content file 2500.

The advantages of this embodiment include:

A search for and removal of clear GIF files will not prevent tracking the digital content file 2500.

Any number of tracking Websites 2506 can be established to confuse any process that attempts to identify and remove these tracking links.

This change is performed by the owner of the digital content, so no copyright violations have occurred.

Excel Plug-in Install Suggestions

Another similar and preferred embodiment uses a clear GIF file to display instructions suggesting that the user install the Excel® plug-in. This GIF file only appears if the Excel® plug-in is not installed on the client opening the Excel file. This process permits a shared Excel® file to educate users about the present invention. Those skilled in the art will develop similar ways to automatically suggest downloading the present invention to protect other types of data, such as Microsoft® Word® and PowerPoint®, and digital content, such as music and movies.

Dynamic Content

Those skilled in the art may use the present invention to keep multiple Excel® files or a single shared Excel® file up-to-date with dynamic content. For example, salesmen opening an Excel® file can always automatically have up-to-the-minute customer status, pricing, and delivery times. The present invention turns Excel® into a dynamic tool with content that is never out-of-date. The present invention turns Excel® into a dynamic tool that is personalized for the current needs of each user.

Those skilled in the art may also use the present invention to make any Microsoft® Office® product or any other product, service, or application a dynamic tool that is never out-of-date and is always personalized. For example, a catalogue in Word® or PDF format could automatically get personalized content from the secure server 204 for the user who has authenticated. This could include his or her favorite color, style, size, shipping preferences, and loyalty program, and so on. This greatly increases the relevance of the catalogue and value of the catalogue service.

Another embodiment of dynamic content is a PDF newsletter that could have a members-only section. Non-members could see an application form for becoming a member. Those skilled in the art may use the present invention to permit digital content to be retroactively controlled after it has been disclosed, something that is currently difficult or next to impossible to achieve.

Data Brokers and Authentication Services

ChoicePoint is an Atlanta-based "data broker" that maintains 19 billion public and private records. Its vision statement says "We strive to create a safer and more secure society through the responsible use of information." Similarly, its mission statement is "To be the most admired information company worldwide" by being "a demonstrated leader in social contribution, to reaffirm our recognition that a corporation must be a positive force in today's society" and by being "a leader in the responsible use of information, to assure that we strike the proper balance between society's right to know and the individual's right to privacy."

ChoicePoint sells sensitive data to its customers to help them reduce the risk of conducting business. At the end of January 2005, an article in the Washington Post called ChoicePoint "an all-purpose commercial source of personal information about Americans, with billions of details about their homes, cars, relatives, criminal records and other aspects of their lives."

ChoicePoint's world changed forever in February 2005 when it was forced to admit that companies had been set up to fraudulently purchase the sensitive data of 145,000 individuals. The immediate fallout included:

An unknown but significant number of individuals had their identities stolen.

A Nigerian man was convicted of fraud for stealing personal information from ChoicePoint.

ChoicePoint's market valuation fell by $700 million.

Several class action lawsuits were filed against ChoicePoint.

The Chairman of the Federal Trade Commission said that ChoicePoint needed to be regulated. In the following year, no laws were introduced that would have prevented the ChoicePoint data theft.

Why Sensitive Data is Collected by Data Brokers and Authentication Services

Figure 26:
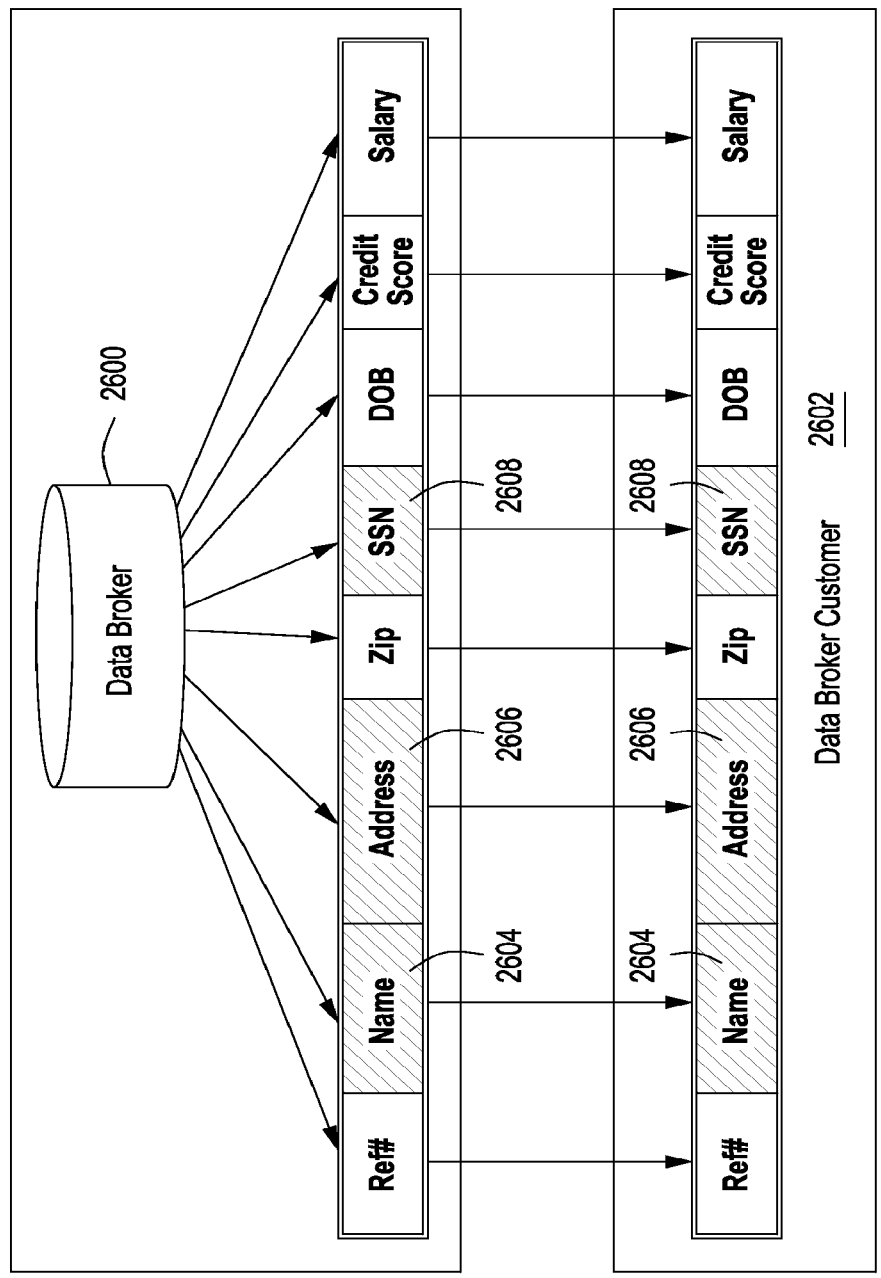
FIGS. 26-32 illustrate protecting sensitive data in a data broker or firm client environment in accordance with one embodiment of the present invention.

Data brokers like ChoicePoint, Equifax, Experian, TransUnion, and LexisNexis collect sensitive data, in part to help their customers mitigate the risk of doing business. In the old days, these companies did business with people they knew. In the digital economy, companies must do business with people they do not know. Data brokers 2600 sell sensitive data to their customers 2602 so that they can make informed decisions about the risks of doing business with individuals and firms they do not know. Referring to FIG. 26, sensitive data is shown in shaded boxes (Name 2604, Address 2604, SSN 2606).

Authentication services like VeriSign collect sensitive data for similar reasons. They pre-screen individuals and firms and give them a digital certificate to authenticate that they are who they say they are. These certificates often contain sensitive data as a part of the authentication process. For this reason, the information passed from authentication services (data broker 2600) like VeriSign to its customers 2602 is similar to data brokers as shown in FIG. 26, although the number and types of fields may be different.

Data broker customers, authentication service customers, and other firms purchase or collect sensitive data in the regular course of doing business. To mitigate business risk, they must have access to sensitive data about prospective customers, employees, trading partners, and so on. It is ironic that knowing that the identity of a consumer has nothing to do with actually making a profit:

ITEMS SOLD times MARGIN/ITEM equals PROFIT

There is nothing in this formula related to sensitive data because the firm makes the same profit irrespective of who the consumer is.

Industry self-regulation has been around since 1996, and new laws have been around since 1998. Both have failed to protect the theft or misuse of sensitive data. This problem will continue to get worse because the amount of information collected is tied directly to the cost of collecting it. And these costs are tied to Moore's Law, which suggests that these costs will continue to fall.

There is a need for a system that manages sensitive data in such a way that mitigates the risk to data brokers, authentication services, their customers, and other firms, without increasing the risks to individuals or firms of having their sensitive data collected, stored, or managed. Moreover, there is a need for a system that manages sensitive data in such a way that firms can make a profit without necessarily having to know the identities of consumers. This would further reduce the risk of having to collect, store, or manage sensitive data.

In the preferred embodiment, sensitive data is controlled by not giving it out in the first place. As Winston Churchill once said, "It's wonderful how well men keep secrets they have not been told."

How the Present Invention Helps Data Brokers and Authentication Services

The present invention provides a system and method that manages sensitive data to minimize the risk to individuals and firms while still providing sufficient information from data brokers and authentication services to their data broker customers.

The present invention provides four new solutions for protecting sensitive data by simply limiting who has access to it. The following table summarizes the benefits:

|  | For Data Brokers and Authentication Services | For Their Customers and for Other Firms |
| --- | --- | --- |
| Centralize and protect sensitive data | Reduce risk | Reduce risk |
| Authentication without sensitive data | Increase revenue | Reduce risk |
| New services to manage sensitive data | Increase revenue | Reduce risk |
| Enterprise system upgrades | Reduce risk | Reduce risk |

While these solutions may be implemented independently, they are shown in the above sequence.

Centralize and Protect Sensitive Data

One major problem is that sensitive data is often stored in multiple places within a firm. For example, ChoicePoint collects and stores information about a person's contact information, marriage history, driving history, motor vehicles, direct marketing history, child support, assets, credit history, and so on. Each of these may contain sensitive data for that person. Another example is that a single bank customer might have a checking account, savings account, mortgage, and car loan, and each may store sensitive data for that customer. This is undesirable for many reasons:

Different copies of sensitive data for any given person may contain different values.

When sensitive data changes, such as when a person moves, the change has to be updated in multiple places. Data synchronization errors occur.

If there are multiple copies of sensitive data, more people may have access to it. For example, it has been reported that over 4 million records were stolen in 2004 from Softbank in Japan. A subsequent analysis revealed that no less than 135 people had access to the sensitive data. Not surprisingly, the analysis was unable to determine how the sensitive data was stolen.

Different copies of the sensitive data can end up in very insecure places. For example, it has been reported that a laptop computer containing 200,000 mortgage customers were stolen from the car of a Wells Fargo consultant. Under California's SB-1386 law, each person had to be notified of the theft. Wells Fargo is said to have paid over $10 million to comply with SB-1386.

When a sensitive data-related law changes or when there is a need to increase the security of sensitive data, the firm has to make these changes everywhere the sensitive data is stored. These costs additional time, require additional money, and dilutes efforts because the firm has to spread its resources to protect sensitive data in more than one location.

The present invention provides a solution to this problem, with the data broker used as an example:

Referring to FIG. 2, a secure server 204 is created to store and protect sensitive data.

Referring to FIG. 4, sensitive systems, table names, and field names are identified for the data broker.

Referring to FIG. 6, sensitive data (2604, 2606 and 2608) is moved to the secure server 204 and a random pointer (2704, 2706 and 2708) replaces it. This process is repeated for each field, record, and table until there is no more sensitive data in the original tables.

Figure 27:
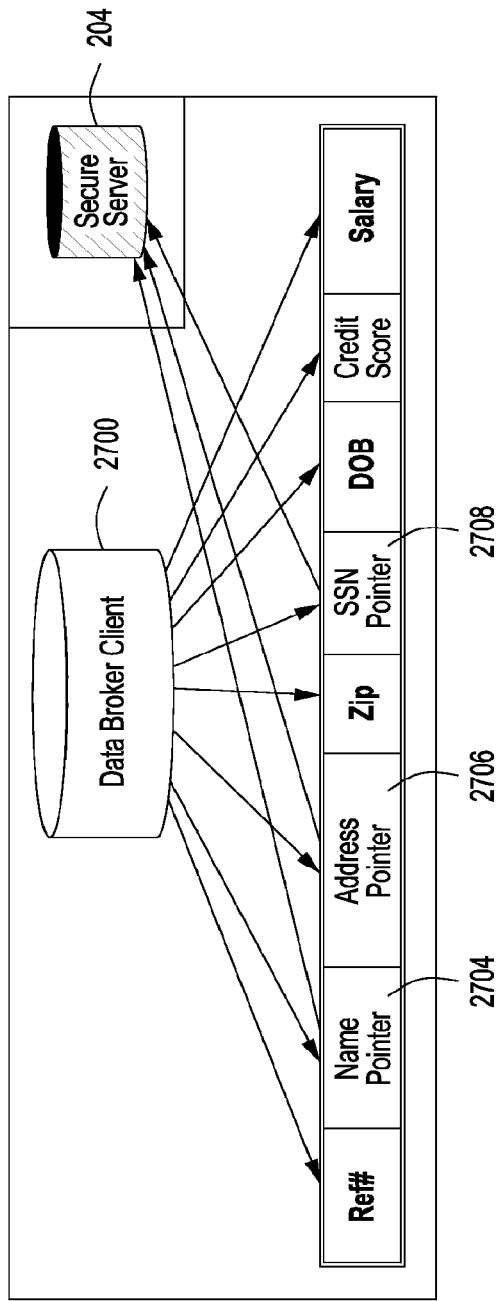

When completed, all sensitive data (2604, 2606 and 2608) is in the secure server 204. Referring to FIG. 27, the data broker's servers and systems are referred to as the data broker client 2700.

Figure 28:
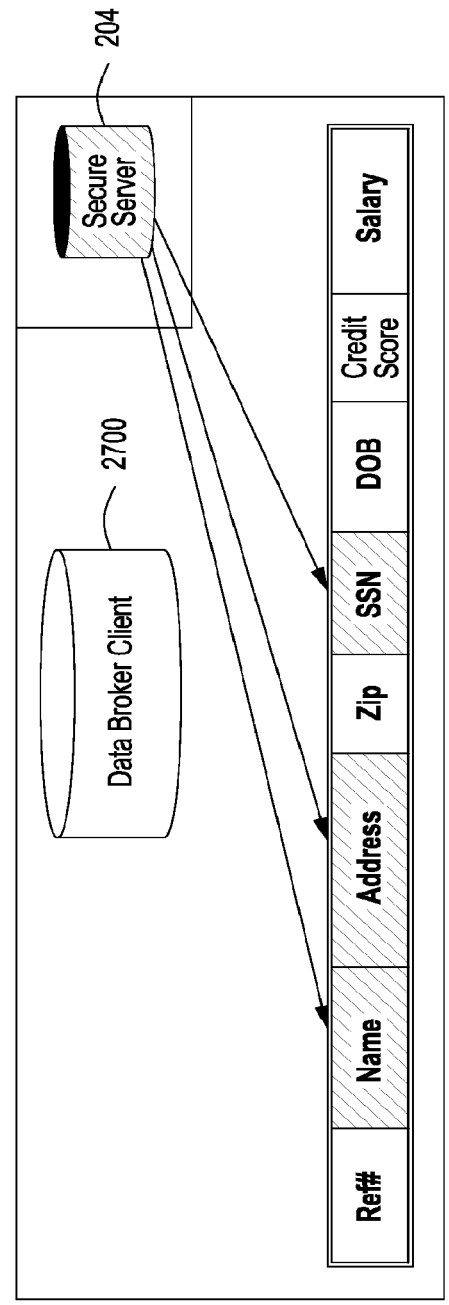

Referring to FIG. 28, each time a record is accessed by data broker client 2700, the pointer (2704, 2706 and 2708) may be used to retrieve sensitive data 2604, 2606 and 2608) from the corresponding field from secure server 204. In this way, the original record can be reconstructed.

Benefits for the data broker (or any firm using the present invention):

Storing all of the sensitive data in one place reduces the risk associated with the collection, storage, and management of sensitive data.

A single copy of sensitive data eliminates data synchronization errors.

The reduced number of systems containing sensitive data means that fewer people have access to it.

Sensitive data is much less likely to end up in very insecure places, such as in laptop computers.

When a related law changes, or when there is a need to increase the security of sensitive data, the data broker has to make changes in only one place.

The data broker can focus all of its attention on protecting the sensitive data in a single location with the best people and resources available.

Authentication without Sensitive Data

Data brokers and authentication services are a part of a multi-billion dollar industry that is under attack. How can any firm collect, store, manage, and then sell sensitive data to data broker customers without running the risk of its fraudulent use? Even the most reputable customer purchasing this sensitive data can be hacked, share data in error, or have it stolen by a rogue employee. As ChoicePoint has shown, a single occurrence may lead to disastrous consequences for a firm, customers, individuals, and society as a whole.

Figure 29:
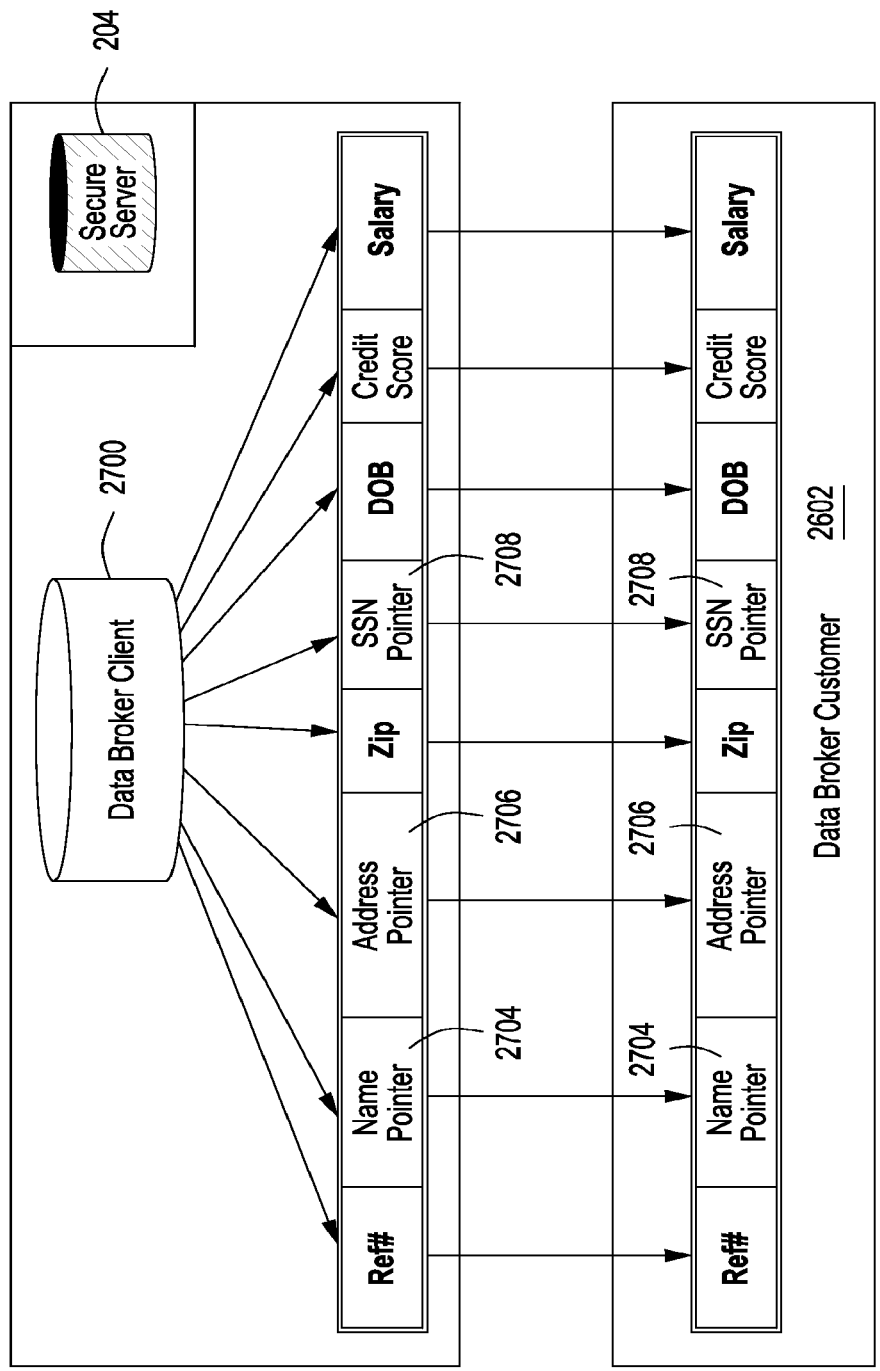

The present invention ensures that sensitive data (2604, 2606 and 2608) is not released to a data broker customer 2602 in the first place. The present invention provides a system that releases data with pointers (2704, 2706 and 2708) to sensitive data (2604, 2606 and 2608) rather than the sensitive data itself. These pointers (2704, 2706 and 2708) validate the existence of these fields, such as SSN, and the possible later access to these fields, without the risks associated with the collection, storage, and management of sensitive data (2604, 2606 and 2608), as shown in FIG. 29.

Benefits for the data broker:

The data broker customer 2602 cannot abuse the sensitive data (2604, 2606 and 2608), even if it wanted to, because the data broker customer 2602 never receives any sensitive data (2604, 2606 and 2608). The sensitive data pointers (2704, 2706 and 2708) that the data broker customer 2602 receives validate that the data broker 2700 has the actual sensitive data (2604, 2606 and 2608) in the secure server 204, but the data broker customer 2602 never actually gets access to the sensitive data (2604, 2606 and 2608) itself. For example, SSN Pointer validates that there is a correct SSN in the secure server 204, but the data broker customer 2602 has no direct access to it (the data broker customer 2602 can instruct the data broker to process the SSN on its behalf, as discussed below). This is a major breakthrough that protects the future viability of data brokers. Reducing these risks decrease the costs of doing business.

Instead of being a part of the privacy problem, data brokers are now a part of the solution. Those that are best at protecting sensitive data will have a sustainable competitive advantage over data brokers that are not.

The data broker has the opportunity to generate new revenue models for new services. For example, the chance of sensitive data being abused by a data broker customer is greatly reduced or even eliminated. The data broker can charge a fee for this. In addition, the data broker can underwrite the risk of the sensitive data being incorrect. A fee can also be charged for this.

Benefits for the data broker customers 2602:

The data broker customer 2602 has outsourced one of the most challenging parts of its business—a part that carries an increasing risk with no corresponding upside potential.

The data broker customer 2602 has the information required to reduce the risk of conducting business with an unknown entity without increasing the risks associated with collecting, storing, and managing sensitive data.

Reducing these risks decreases the data broker customer's cost of doing business.

The data broker customer 2602 can focus on what it does best—increasing items sold and margins.

This example is for data brokers. Those skilled in the art will use the present invention to work for any firm, including authentication firms such as VeriSign, so that they can offer certificates or some other service that validate the identity of an entity without revealing any sensitive data.

In addition to pointers that are random, another preferred embodiment is a reference number of each record passed from the data broker to the data broker customer may include the following:

Customer code uniquely identifies the data broker customer and is used to validate subsequent requests from this customer to ensure that, for example, the data has not been stolen from another data broker customer.

Customer number uniquely identifies the actual customer for this data broker customer and is needed because other applications may store other records for this actual customer, either locally, at the original data broker, or at another data broker. This "persistent" customer number may be assigned by the data broker customer and remains the same in all applications in all locations.

Control number may be used by the data broker or data broker customer for version control, hashing, or any other control purpose.

New Services to Manage Sensitive Data

In addition to helping data broker customers reduce risk, data brokers currently sell sensitive data so that their data broker customers can increase their profits. For example, names and addresses may be sold so that data broker customers 2602 can send promotional material to prospects. But this creates problems:

As recent events have shown, sensitive data in the hands of data broker customers can be abused. Even the most reputable firms have rogue employees, and sensitive data only has to be stolen once for lives to be ruined.

The risks associated with collecting a, individual's sensitive data could one day be more than the lifetime value of that individual. If this occurs, the firm's very survival could be put at risk.

When sensitive data is sold, it is usually under certain terms and conditions. For example, names and addresses may be sold to be used for a specific time period or a limited number of times. Data brokers "seed" this data with fake names for the sole purpose of auditing how this data is used. This is problematic because (1) it's after-the-fact and too late to protect the abuse, and (2) it represents lost revenue for the data broker.

The unique solution to this problem is the data broker customer passing requests back to the data broker (or some other trusted third party) for further processing:

The reference number (or some other unique identifier) is passed by the data broker customer back to the data broker.

Also passed back are instructions and, optionally, some other material. For example, this could be "send the attached brochure to all of these people using first class mail" or "do a certain analysis for all people with a SSN beginning with 344."

Figure 30:
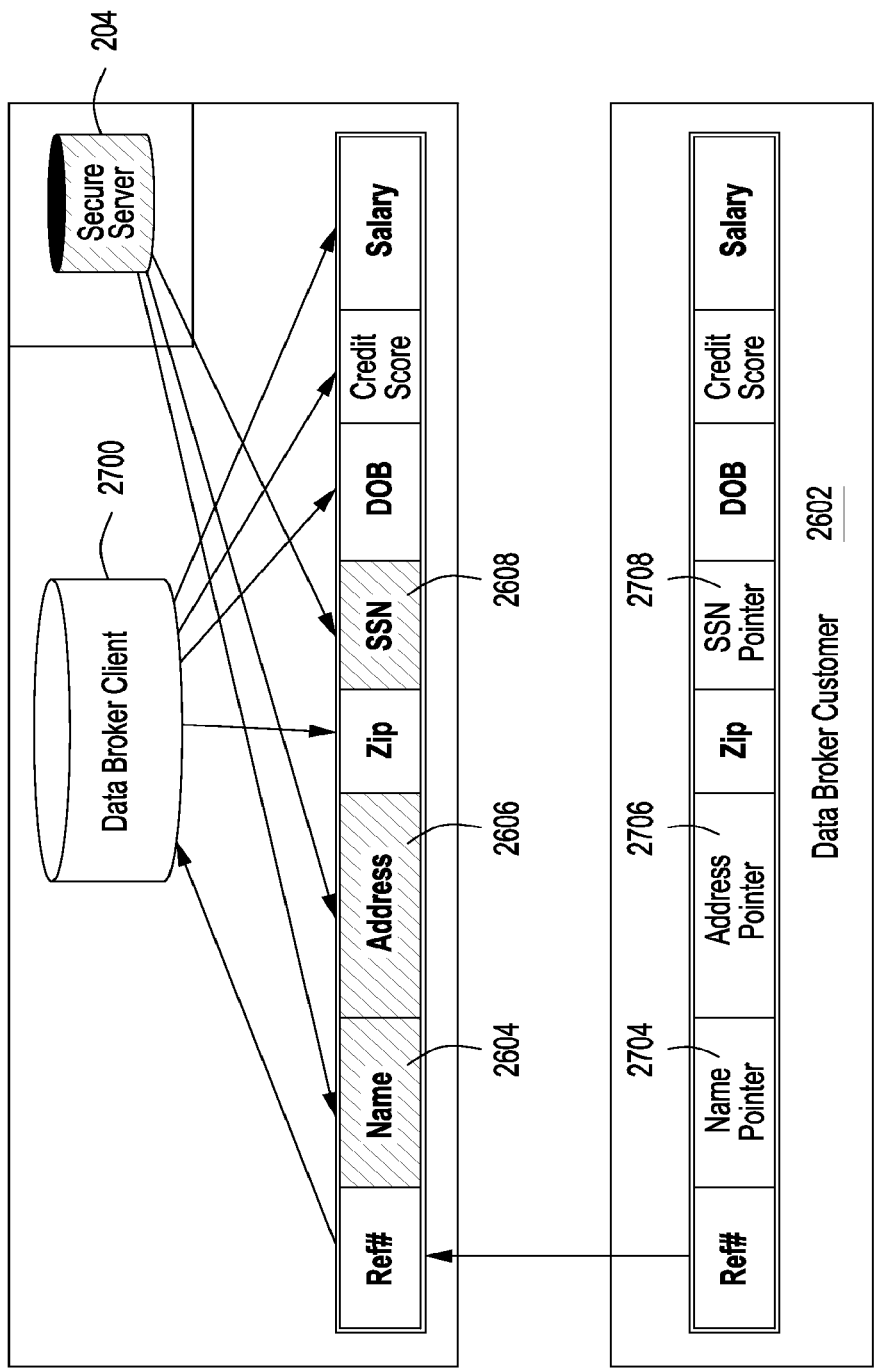

Referring to FIG. 30, the data broker uses the reference number to recreate the original record or parts of the original record. This is done by using the reference number to validate the request and the retrieve the data from data broker server and sensitive data from the secure server 204. When this is completed, the data broker processes the record according to the data broker customer's instructions.

Benefits for the data broker:

Because the data broker is the only party that knows how to convert reference number into the actual sensitive data, all sensitive data is always under the direct control of the data broker.

For the same reason, the data broker has new "baked in" revenue models. These include fulfillment (mailing promotional materials), further analysis that includes examining sensitive data data, ensuring that the desired results are correct, and so on.

If data is stolen from the data broker customer, any receiving party can only act upon the stolen data by making a request to the data broker. When this happens, (1) the data broker can reject the request and (2) notify the data broker customer that it has a security problem. This self-auditing process is a major benefit of the present invention. In no case is the sensitive data at risk when data is stolen.

The economies of scale permit the data broker to manage data broker customer requests in a much more efficient manner than by any single firm. This means that data brokers have higher margin potential as their business grows.

Benefits for data broker customers:

Again, the data broker customer has outsourced one of the most challenging parts of its business—a part that carries an increasing risk without any corresponding upside potential.

The data broker customer has the information required to reduce the risk of conducting business with an unknown person without increasing the risk's associated with collecting, storing, and managing sensitive data.

The concept of outsourcing all work related to sensitive data has the potential to free the data broker customer of liabilities associated with sensitive data. This could include order entry, payment processing, order fulfillment, help desks, and all other commodity services that are not core to the data broker customer's mission.

The data broker customer can focus on what it does best—increasing items sold and margins.

This example is for data brokers. Those skilled in the art will use this same methods or process to work for any firm, including authentication firms such as VeriSign, so that it can offer certificates that validate the identity of a person without revealing any sensitive data. Authentication without identification would give firms like VeriSign, new revenue model opportunities.

Enterprise System Upgrades

Regulations for running an enterprise are constantly changing. In addition, the liabilities associated with collecting, storing, and managing sensitive data continues to increase. And Moore's Law suggests that this will increase at an accelerated rate.

These problems are a major concern for firms with large enterprise systems. As the Y2K problem showed, it can cost tens of millions of dollars to upgrade an enterprise system. The main difference between the Y2K problem and the management of sensitive data is that Y2K was a one-time problem, whereas problems related to data theft and new regulation compliance is ongoing. It would be highly desirable if there was a way for a firm to gain control of the management of sensitive data so that changes from new regulations and risks could be dealt with in a more timely and cost-effective manner. Another embodiment of the present invention provides such a solution.

Figure 31:
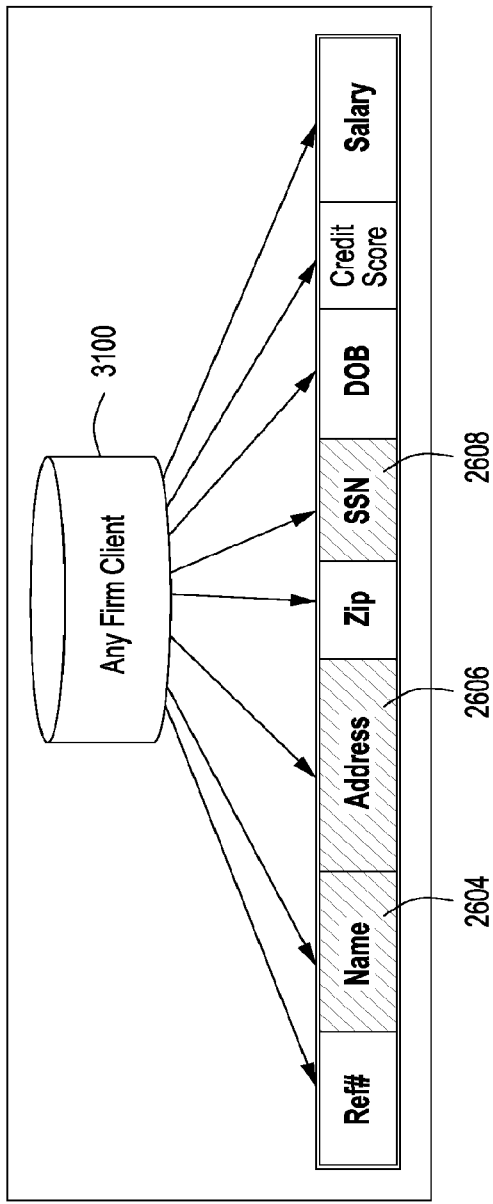

Referring to FIG. 31, any firm 3100 has the same problems managing sensitive data as data brokers have. The solution to this is similar to the solution previously described for data brokers.

Figure 32:
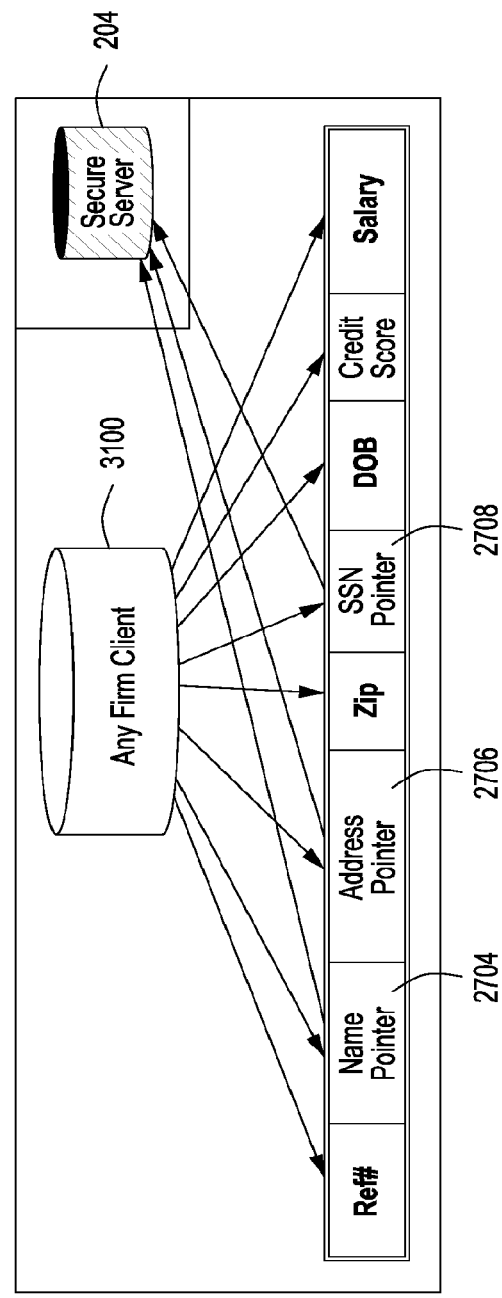

Referring to FIG. 32, all fields containing sensitive data (2604, 2606 and 2608) are identified, the contents are moved to a new secure server 204, and the original field has a random pointer (2704, 2706 and 2708) inserted that points to the new location of the sensitive data (2604, 2606 and 2608).

Care must be taken to ensure that the new pointer information is the same type as the sensitive data field that it is replacing. This will help make these changes transparent to the file management system used by the enterprise system. For example, a 9-digit SSN stored in ASCII text should be replaced with a 9-digit or less pointer also stored in ASCII text.

The applications that access the enterprise system may be modified with plug-ins and database triggers as previously described.

Another preferred embodiment is changing application code that manages sensitive data from:
move CUSTOMER-SSN to PRINT-SSN
... to:
move sensitivedata(CUSTOMER-SSN) to PRINT-SSN
... where "sensitivedata" is a new function that performs certain tasks:
  Authentication that the application and user running this application is permitted access to SSN.
  Ensuring that the reason for and usage of the SSN confirms with best practices, legal requirements and operational procedures, as defined by plug-ins.
  Using the SSN pointer to access the correct SSN data in secure server 204.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims.

What is claimed is:

1. A system for protecting sensitive data comprising:
one or more clients, each client having a respective processor and a respective data storage device communicably coupled to its respective processor; and
a server communicably coupled to the one or more clients;
wherein a first one of the clients and the server protect sensitive data items stored by the first one of the clients in a respective first data storage device by restricting subsequent access to and use of the sensitive data items by:
  the first one of the clients replacing the sensitive data items with one or more pointers received from the server, the one or more pointers comprising non-sensitive data of a same data type as the sensitive data and indicating one or more locations where the sensitive data items have been stored in a secure storage by the server,
  a respective first processor of the first one of the clients receiving a first request for data,
  the first processor determining whether the first request requires one or more items of sensitive data,
  the first processor providing the requested data from a respective first storage device of the first one of the clients when the first request does not require sensitive data, otherwise
  performing the following steps when the first request requires the one or more sensitive data items:
    the first one of the clients sending a second request containing one or more pointers to the server, the server authenticating the second request,
    the server denying the second request when the authentication fails, and
    the server providing the one or more sensitive data items corresponding to the one or more pointers included in the second request when the authentication succeeds.

2. The system of claim 1, wherein the sensitive data items comprise at least one of: personal data, financial data, corporate data, legal data, government data, police data, immigration data, military data, intelligence data, security data, surveillance data, technical data, copyrighted content or a combination thereof.

3. The system of claim 1, wherein: each client comprises a respective one of: a computer, a laptop computer, a handheld computer, a desktop computer, a workstation, a data terminal, a phone, a mobile phone, a personal data assistant, a media player, a gaming console, a security device, a surveillance device or a combination thereof; and the server is communicably coupled to each respective one of the one or more clients via a respective computer network, a telecommunications network, a wireless communications link, a physical connection, a landline, a satellite communications link, an optical communications link, a cellular network or a combination thereof.

4. The system of claim 1, wherein communications between the server and one or more of the one or more clients are encrypted.

5. A method for protecting sensitive data comprising:
receiving, at a server communicably coupled to one or more clients, first extracted data from a first one of the clients, storing the first extracted data at locations in a secure storage indicated by pointers, and sending to the first one of the clients the pointers,
at the first one of the clients, replacing the extracted data with the pointers, wherein the extracted data comprises one or more items of sensitive data and the pointers comprise non-sensitive data of a same data type as the sensitive data;
receiving, at the server, a first request for data,
determining, by the server, whether the first request requires the one or more items of sensitive data, and
if the first request does not require the one or more items of sensitive data, providing the requested data, and otherwise, if the first request does require the one or more items of sensitive data, receiving a second request containing one or more of the pointers, authenticating the second request, denying the second request when the authentication fails, and otherwise providing the one or more sensitive data items corresponding to the one or more pointers included in the second request when the authentication succeeds.

6. The system of claim 5, wherein the sensitive data items comprise at least one of: personal data, financial data, corporate data, legal data, government data, police data, immigration data, military data, intelligence data, security data, surveillance data, technical data, copyrighted content or a combination thereof.

7. The system of claim 5, wherein: each client comprises a respective one of: a computer, a laptop computer, a handheld computer, a desktop computer, a workstation, a data terminal, a phone, a mobile phone, a personal data assistant, a media player, a gaming console, a security device, a surveillance device or a combination thereof; and the server is communicably coupled to each respective one of the one or more clients via a respective computer network, a telecommunications network, a wireless communications link, a physical connection, a landline, a satellite communications link, an optical communications link, a cellular network or a combination thereof.

8. File system of claim 5, wherein communications between the server and one or more of the one or more clients are encrypted.

\* \* \* \* \*